United States Patent [19]

DeMoranville et al.

[11] Patent Number: 5,355,304
[45] Date of Patent: Oct. 11, 1994

[54] CLINICAL LABORATORY WORK-FLOW SYSTEM WHICH SEMI-AUTOMATES VALIDATED WHICH SEMI-AUTOMATES VALIDATED IMMUNOASSAY AND ELECTROPHORESIS PROTOCOLS

[76] Inventors: Victoria E. DeMoranville, 22 Forge Rd., Assonet, Mass. 02702; James E. Ellis, 23 Ephriam Dr., Mansfield, both of Mass. 02048

[21] Appl. No.: 477,265

[22] Filed: Jan. 30, 1990

[51] Int. Cl.$^5$ .............................................. G06F 15/00
[52] U.S. Cl. ........................... 364/413.02; 364/413.01
[58] Field of Search .................... 364/413.02; 422/63, 422/65, 67, 62; 436/808; 73/864.21

[56] References Cited

U.S. PATENT DOCUMENTS

| | | | |
|---|---|---|---|
| 3,951,605 | 4/1976 | Natelson | 422/67 |
| 4,259,288 | 3/1981 | Welch | 422/67 |
| 4,559,120 | 12/1985 | Royse et al. | 204/182.8 |
| 4,816,418 | 3/1989 | Mack et al. | 422/65 |
| 4,827,780 | 5/1989 | Sarrine et al. | 73/864.21 |
| 4,927,545 | 5/1990 | Roginski | 422/67 |
| 4,931,402 | 6/1990 | Abplanalp | 435/291 |

*Primary Examiner*—Roy N. Envall, Jr.
*Assistant Examiner*—Ari M. Bai
*Attorney, Agent, or Firm*—Nicholas I. Slepchuk; Arthur S. Morgenstern

[57] ABSTRACT

A multi-tasking clinical laboratory work-flow system for test sample and reagent transfer to semi-automate various laboratory assays. The system includes a controller having a menu of protocols which provide format instructions to a robotic sample transfer device. The sample transfer device includes a work-flow surface (deck) having defined coordinates for mounting one or more test racks and one or more reaction mediums, and means for interacting a test sample with one or more reagent(s) or gel in a reaction medium.

34 Claims, 36 Drawing Sheets

Small Clinic
System Configuration: RSP 5051 MLAII

| Summary | Before | After |
|---|---|---|
| Number of Methodologies | 4 | 4 |
| Number of Assays | 7 | 5 |
| Total Run Time | 8hrs. | 3.5hrs. |
| Number of FTE's | 1 | .5 |
| Number of Tubes | 345 | 345 |
| Annual Labor Dollars Saved* | 0 | $11,000 |
| Increased Annual Opportunity Value† | 0 | $109,950 |

*Assumption is labor for 1 FTE per year = $22,000

†Industry average, 1 FTE can generate $18,325 in revenue per month

Conclusions:
- Labor has been reduced by 50%
- Turn around time has been improved by 4.5 hrs.
- Run time has been cut by 56%
- Payback for the system is less than 1 yr.

FIG. 2d

Medium to Large Hospital: One Technician

System Configuration: Electrophoresis Enhanced System

| Summary | Before | After |
|---|---|---|
| Number of gels set up at one time | 1 | 9 |
| Number of results in 4 hours (including controls) | ? | 152 |
| Pipetting time saved during 4 hours | 0 | 53min |

Conclusions:

- More fexible work flow
- Can set up more than one chemistry simultaneously
- 152 answers from 4 different chemistries in 4 hrs. using one technician

FIG. 3d

Large Hospital Laboratory
600 Beds

System Configuration: RSP 5051 Genesys 25 well

| Summary | Before | After | Conclusions |
|---|---|---|---|
| Number of Methodologies | 8 | 8 | • Labor has been reduced by 42% |
| Number of Assays | 8 | 8 | • Turn around time has been improved by 4.5 hrs. |
| Total Run Time | 8 hrs. | 3.5 hrs. | • Run time has been cut by 56% |
| Number of FTE's | 1.2 | .5 | • Payback for the system is less than 1 year |
| Number of Tubes | 299 | 299 | |
| Annual Labor Dollars Saved* | 0 | $15,400 | |
| Increased Annual Opportunity Value† | 0 | $153,930 | |

\* Assumption is labor for 1 FTE per year = $22,000

† Industry average, 1 FTE can generate $18,325 in revenue per month

FIG. 4d

Large Reference Lab
West Coast

System Configuration: RSP 5052 Genesys 25 Well

| Summary | Before | After | Conclusions |
|---|---|---|---|
| Number of Methodologies | 2 | 2 | • Labor has been reduced by 50% |
| Number of Assays | 11 | 11 | • Turn around time has been improved by 3hrs. |
| Total Run Time | 8 hours | 5 hours | • Run time has been reduced by 38% |
| Number of FTE's | 1.5 | 1 | • Payback for the system is less than 1 year |
| Number of Tubes | 1800 | 1800 | |
| Annual Labor Dollars Saved* | 0 | $11,000 | |
| Increased Annual Opportunity Value† | 0 | $109,950 | |

*Assumption is labor for 1 FTE per year = $22,000
†Industry average, 1 FTE can generate $18,325 in revenue per month

FIG. 5e

Medium Sized Reference Lab

System Configuration: RSP 5051 Genesys 25 well

| Summary | Before | After |
|---|---|---|
| Number of Methodologies | 9 | 9 |
| Number of Assays | 21 | 11 |
| Total Run Time | 8hrs. | 6hrs. |
| Number of FTE's | 3 | 1 |
| Number of Tubes | 1008 | 1008 |
| Annual Labor Dollars Saved* | 0 | $44,000 |
| Increased Annual Opportunity Value† | 0 | $439,800 |

\* Assumption is for 1 FTE per year = $22,000
† Industry average, 1 FTE can generate $18,325 in revenue per month

Conclusions

- Labor has been reduced by 2 FTE's
- Turn around time has been improved by 2 hrs.
- Run time has been reduced by 25%
- Payback for the system is less than 1 year

FIG. 8f

CLINICAL LABORATORY WORK-FLOW SYSTEM WHICH SEMI-AUTOMATES VALIDATED WHICH SEMI-AUTOMATES VALIDATED IMMUNOASSAY AND ELECTROPHORESIS PROTOCOLS

This application includes a microfiche appendix which contains three sheets of microfiche having a total of two hundred frames. The microfiche or paper copies thereof are available for public inspection and also separately available for purchase from Ciba Corning Diagnostics Corp., 63 North Street, Medfield, Mass. 02052. Requests for public inspection and for purchase of the microfische or paper copies thereof are to be made in writing to the Steinberg Information Center of Ciba Corning Diagnostics Corp. The requests should specify the title of the patent and the above listed patent number.

BACKGROUND OF THE INVENTION

1. Field of the Invention

The present invention relates to a multi-tasking clinical laboratory work-flow system and, more particularly, to a system incorporating a robotic sample transfer device(s); and which semi-automates validated immunoassay and electrophoresis protocols.

2. Setting for the Invention

Most clinical laboratories today, and in the foreseeable future, are faced with becoming more efficient. The quest for efficiency, however, is confronted with the decreasing availability of trained laboratory technologists and an expanding menu of diagnostic testing protocols. Generally, becoming more efficient means increasing or maintaining the timely output of test results with the same number or fewer technologists, i.e. hands-on labor.

The overused and sometimes misused solution to the quest for efficiency has been automation. Automation in the laboratory usually means optimizing work-flow to increase output, shortening turn-around time in reporting test results, while utilizing less labor, i.e. fewer full-time equivalents (FTE). Attempts to accomplish these objectives have focused on applying the use of instrumentation, computers and manual activities. The application of automation, however, has not achieved, for all laboratories, the expected improvements in efficiency.

One explanation that is generally expressed to account for the lower than expected improvements in efficiency is the variation of work-flow demands in many laboratories. Consequently, automation does not always mean replacing every manual activity in the laboratory. This problem is further propounded by the inability of instrumentation systems to accommodate changes in the daily work-flow patterns of the laboratory. In addition, a thorough analysis of work-flow patterns is generally neglected before attempts are made to enhance work-flow.

The use of robotics in the laboratory has been examined as one way to optimize work-flow and thus increase efficiency. The use of robotics, in most cases, requires the conversion of human-assisted (manual) protocols to robotic-assisted (semi-automated) protocols. This conversion requires training of the involved technologists and the integration of the robotic device into the laboratory.

OBJECTIVES OF THE INVENTION

Accordingly, it is a primary object of the present invention to provide a multi-tasking work-flow system, which includes a robotic sample transfer device, which semi-automates validated immunoassay and electrophoresis testing in a clinical laboratory.

It is another objective of the present invention to provide a robotic sample applicator for electrophoresis testing, which enables the automated application of a defined volume of a test sample onto a gel.

It is a further objective of the present invention to provide an electrophoresis deck for use on a robotic sample transfer device, which can be leveled within a tolerance of 0.01 mm.

It is an object of the invention to provide a robotic system for semi-automating diagnostic assays which eliminates sample processing problems associated with accurately and precisely dispensing test samples, sample carry-over, and end of run drift.

It is still another object of the invention to provide computer program(s) means for controlling the use of robotics in performing validated immunoassay and electrophoresis protocols.

A further object of the invention is to provide a robotic sample transfer device for electrophoresis testing to eliminate manual test technique variations in applying a test sample onto a gel.

A further object of the invention is to provide an adapter plate for an electrophoresis deck of a robotic sample transfer device which allows for easy transition from electrophoresis to immunoassay testing.

It is still a further object of the invention to provide a multi-tasking system for diagnostic immunoassays and electrophoresis testing, which achieves efficient work-flow savings in labor, test sample turn-around time, protocol run time and increased annual financial opportunity.

Yet another object of the invention is to provide a robotic sample transfer device to transfer a test sample and one or more reagents for protocols that were designed to be run manually, and achieve diagnostically the same test results as one would have received from the manual performance of the protocol.

With these and other objects in view, as will be apparent to those skilled in the art, the invention resides in the combination of parts set forth in the specification, including the microfische appendix, and covered by the claims appended hereto.

SUMMARY OF THE INVENTION

In general, the invention consists of a semi-automated multi-tasking clinical laboratory work-flow system, which includes a robotic sample transfer device. A system controller provides a menu of validated immunoassay and electrophoresis protocols which may be selected by the system user in accordance with their work-flow demands. Following selection of a test protocol and entry of the number of test samples to be analyzed, the controller will display an order sequence for arranging test sample containers in one or more test racks. The racks are then positioned on a work-flow surface (deck) of the robotic transfer device, at specific coordinates, such that the position of the sample container(s) are recognized by one or more sample applicators of the robotic sample transfer device. One or more reaction medium(s) are also mounted on the deck at specific coordinates. The reaction medium provides a site for interacting each test sample and one or more reagent(s). The robotic sample transfer device in response to instructions from the controller transfers a volume of test sample and one or more reagent(s) to a reaction medium for immunoassay protocols. In the electrophoresis protocols a volume of test sample of about 1 ul. is transferred onto a reaction medium. The reaction medium(s) and test racks are then removed from the deck for subsequent processing to effect a test result.

Test results for each test sample are detected by conventional detection devices which are specific for the selected protocol. Test data is reported according to established practices of the laboratory.

The system, following a work-flow demand analysis, may be rapidly integrated in a variety of clinical laboratories to effect savings in labor (FTE), test sample turn around time, protocol run time, and increasing annual financial opportunity. The multi-tasking capabilities of the system allows each user laboratory to develop their own work-flow to maximize throughput.

The system includes software programs for a plurality of validated test protocols. Each test protocol in the system was validated for precision, accuracy, carryover, end run drift, and in comparison to manual performance of the protocol.

The electrophoresis deck is specifically designed such that the planar axis thereof may be adjusted to tolerance levels within 0.01 mm. The deck for the immunoassay testing is adapted to be mounted onto the electrophoresis deck when an immunoassay protocol is selected.

The present invention provides:

A clinical laboratory work-flow system which semi-automates validated immunoassay and electrophoresis protocols, said system having components including:
 a controller for directing the operation of said system, said controller comprising:
  a memory unit having a plurality of computer programs stored therein, each of said programs providing format instructions for performance of a specific immunoassay or electrophoresis protocol;
  means for selecting a protocol;
  means for entering the number of test samples to be analyzed by said protocol;
  means for displaying the format instructions for said protocol, wherein the format instructions define one or more test rack(s) and reaction medium(s) to be utilized for performing said protocol, each test rack being adapted to receive a sequence of ordered test sample containers each of which contain a volume of test sample, the format instructions further defining the sequence of ordering the test containers in the test rack(s) in accordance with the number of test samples entered, and;
 a robotic test sample transfer device comprising:
  a planar work-flow surface having a defined coordinate area for receiving and aligning test rack(s) and reaction medium(s); and
  means for transferring a volume of test sample for each test sample to be analyzed, and a volume of one or more reagent(s) from a reagent source(s) for immunoassay protocols, to a reaction medium for initiating a test reaction, the transfer(s) being in response to format instructions from said controller, and wherein said transfer(s) are free of sample carryover and free of end run effect.

The present invention further provides:

A clinical laboratory work-flow system which semi-automates validated electrophoresis testing including:
 a controller comprising:
  a memory unit having a plurality of computer programs stored therein, each of said programs providing format instructions for performance of a specific or electrophoresis protocol;
  means for selecting a protocol;
  means for entering the number of test samples to be analyzed by said protocol;
  means for displaying the format instructions for said protocol, wherein the format instructions define one or more test rack(s) and reaction medium(s) to be utilized for performing said protocol, each test rack being adapted to receive a sequence of ordered test sample containers each of which contain a volume of test sample, the format instructions further defining the sequence of ordering said test containers in accordance with the number of test samples entered, and;
 a robotic test sample transfer device comprising:
  a work-flow surface having a defined coordinate area for receiving and aligning said test rack(s) and reaction medium(s), said surface being adjustable, and wherein said reaction medium is an electrophoresis gel; and
  transfer means for applying about 1 ul. of test sample onto said gel.

BRIEF DESCRIPTION OF THE DRAWINGS

FIGS. 2a–2d are work-flow analysis diagrams of the system as integrated in a small clinic.

FIGS. 3a–3d are work-flow analysis diagrams of the system as integrated in a medium to large hospital utilizing one (1) technician.

FIGS. 4a–4d are work-flow analysis diagrams of the system as integrated in a large hospital.

FIGS. 5a–5e are work-flow analysis diagrams of the system as integrated in a large reference laboratory.

FIGS. 8a–8f are work-flow analysis diagrams of the test system as integrated in a medium-sized reference laboratory.

DESCRIPTION OF THE PREFERRED EMBODIMENT

The figures summarize a series of case studies which demonstrate the multi-tasking application of the system. The dark or shaded areas of the work-flow diagrams depict hands-on time for the FTE(s), while the clear areas depict hands-off time. The horizontal axis of the figures shows a time line (hour) for the operation of the system and the vertical axis shows the number of assays and methodologies being performed in the particular case study. The work-flow analysis shows the steps required in the performance of the selected protocol. It is noted that the abbreviation "AB" means the addition of antibody to the reaction medium for immunoassay protocols. The abbreviation "RSP" means robotic sample processor.

A legend is provided for each case study, which presents a comparison of results before and after the integration of the system at the test site. The results include the number of methodologies, number of test assays, total run time, number of FTE's, number of tubes, labor dollars saved, and increased annual opportunity. The labor dollars saved and increased annual opportunity are based on the assumption that labor for one FTE per year equals twenty-two thousand dollars (U.S.) ($22,000.00) and that one FTE can generate eighteen thousand three hundred and twenty-five dollars (U.S.) ($18,325.00) in revenue per month. It is understood that variations in these values will effect the financial data noted in the legend.

The legend for each case study also provides a summary of conclusions for the study, and generally includes the percentage of labor reduction, the improvement in test sample turn around time, the percentage reduction in protocol run time, and payback time for the system.

Figure 1:
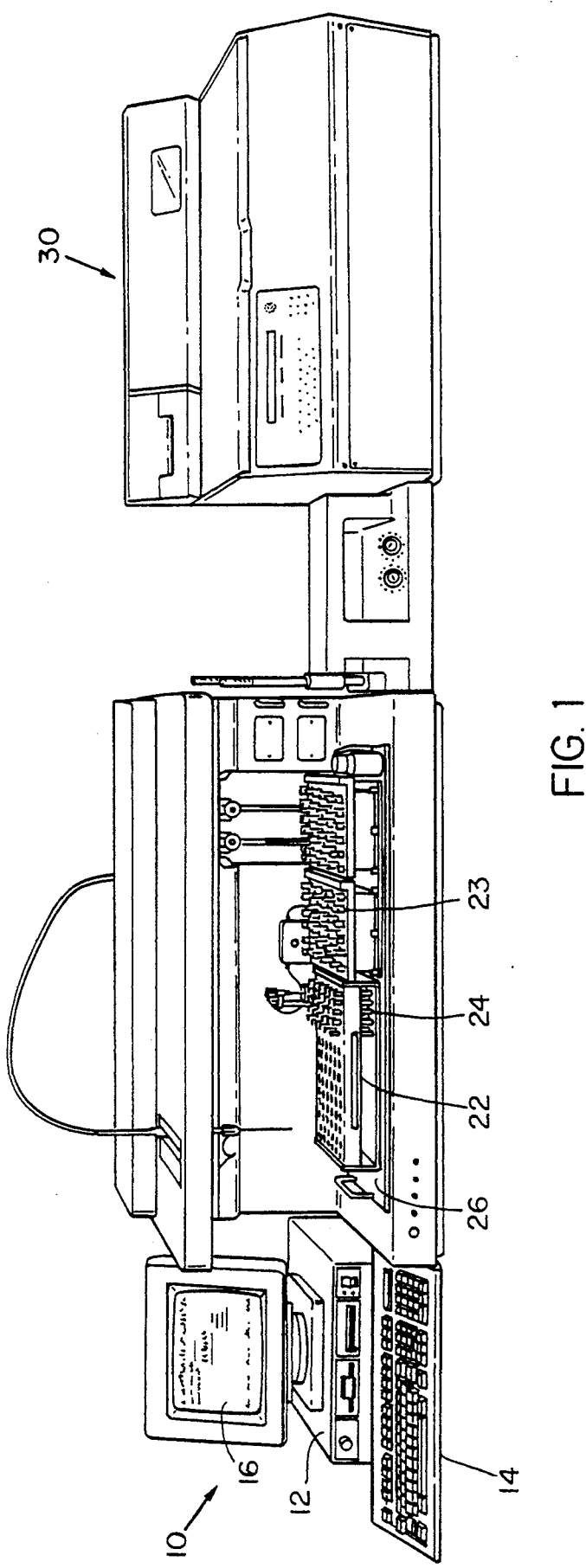
FIG. 1 is a perspective view, in one form, of the components of the work-flow system of the present invention.
Figure 2A:
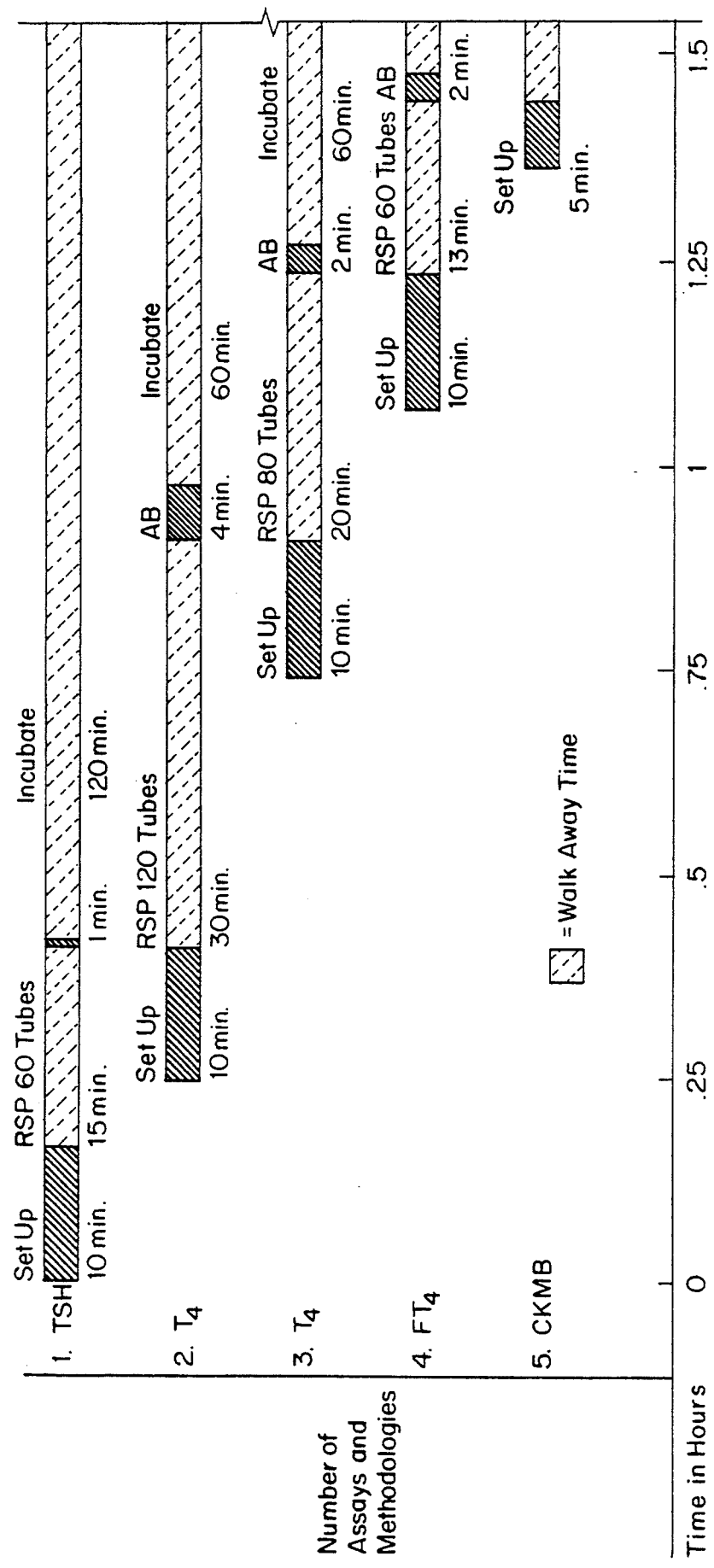
Figure 2B:
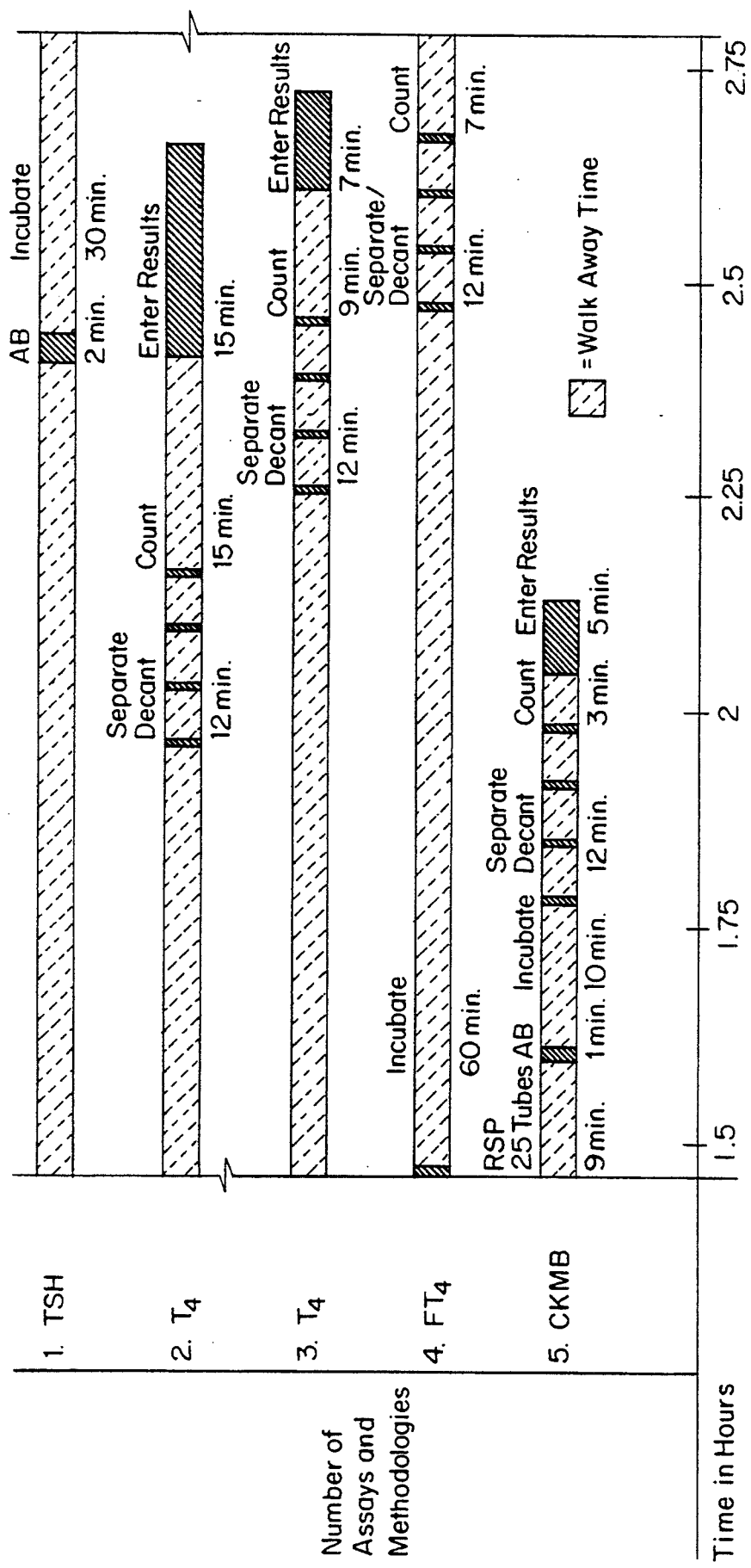
Figure 2C:
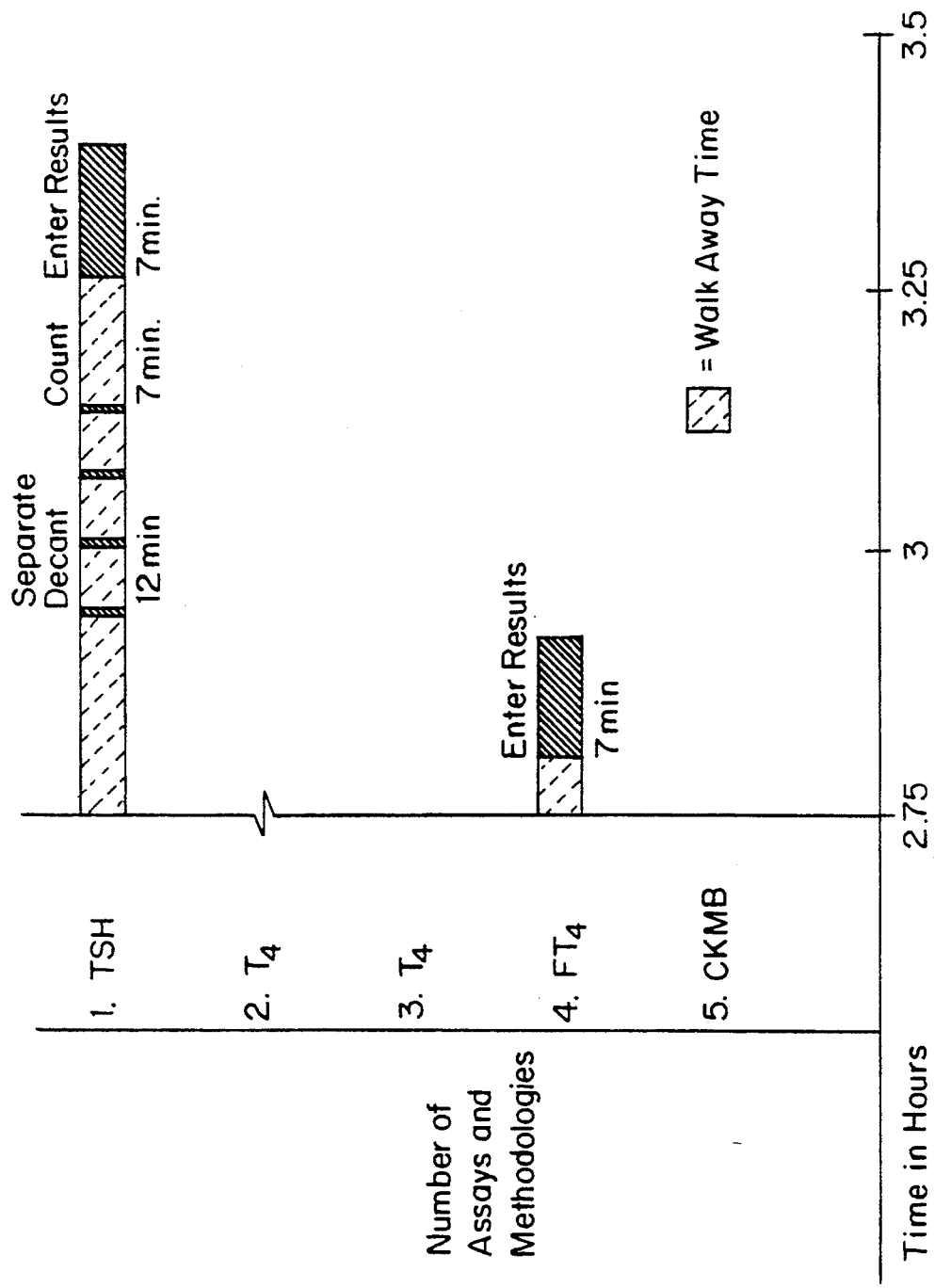
Figure 3A:
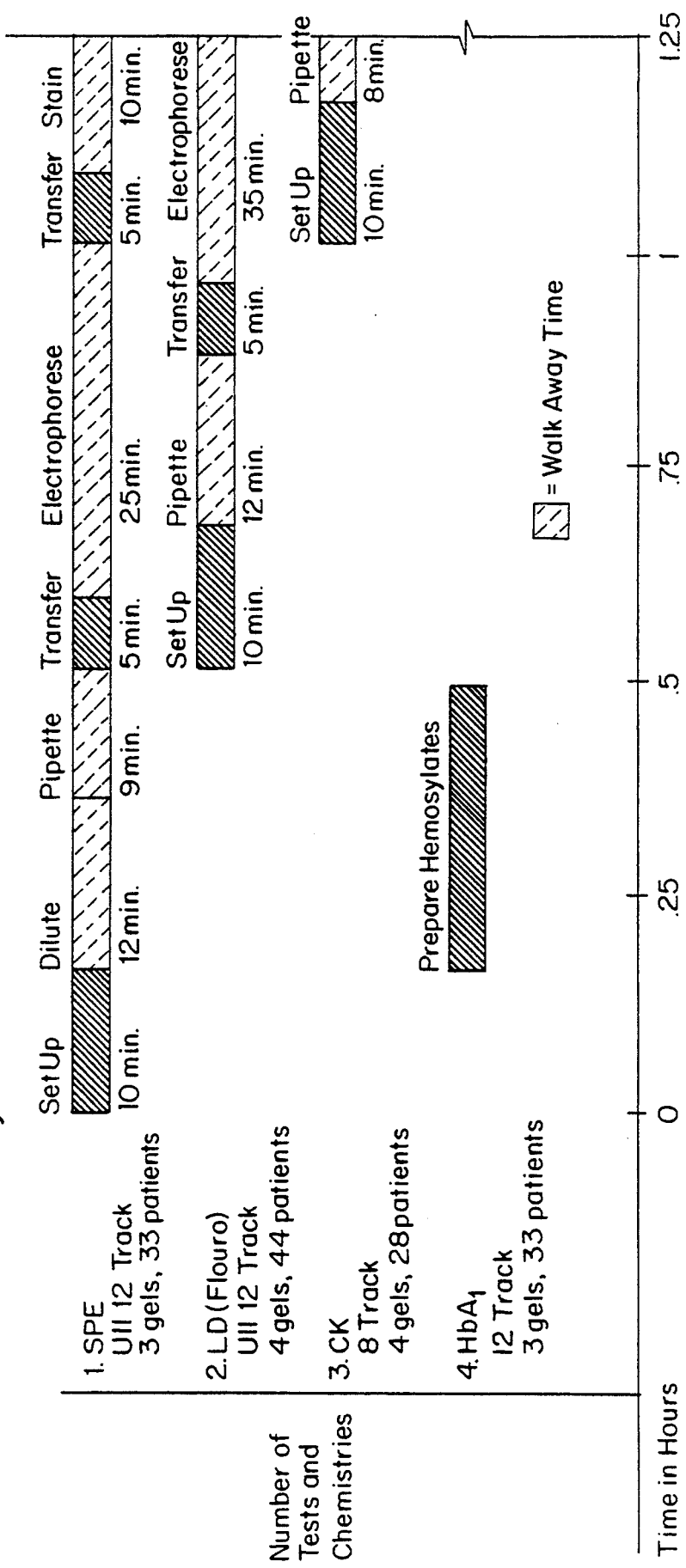
Figure 3B:
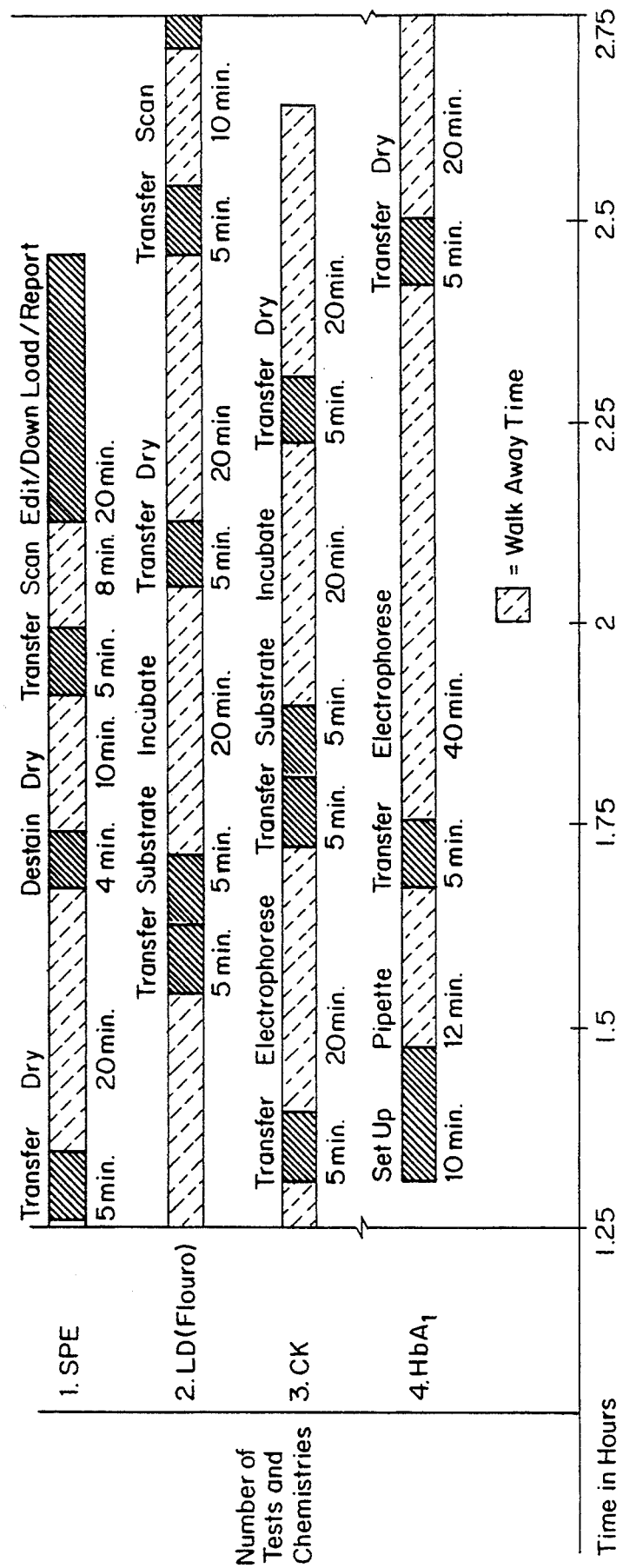
Figure 3C:
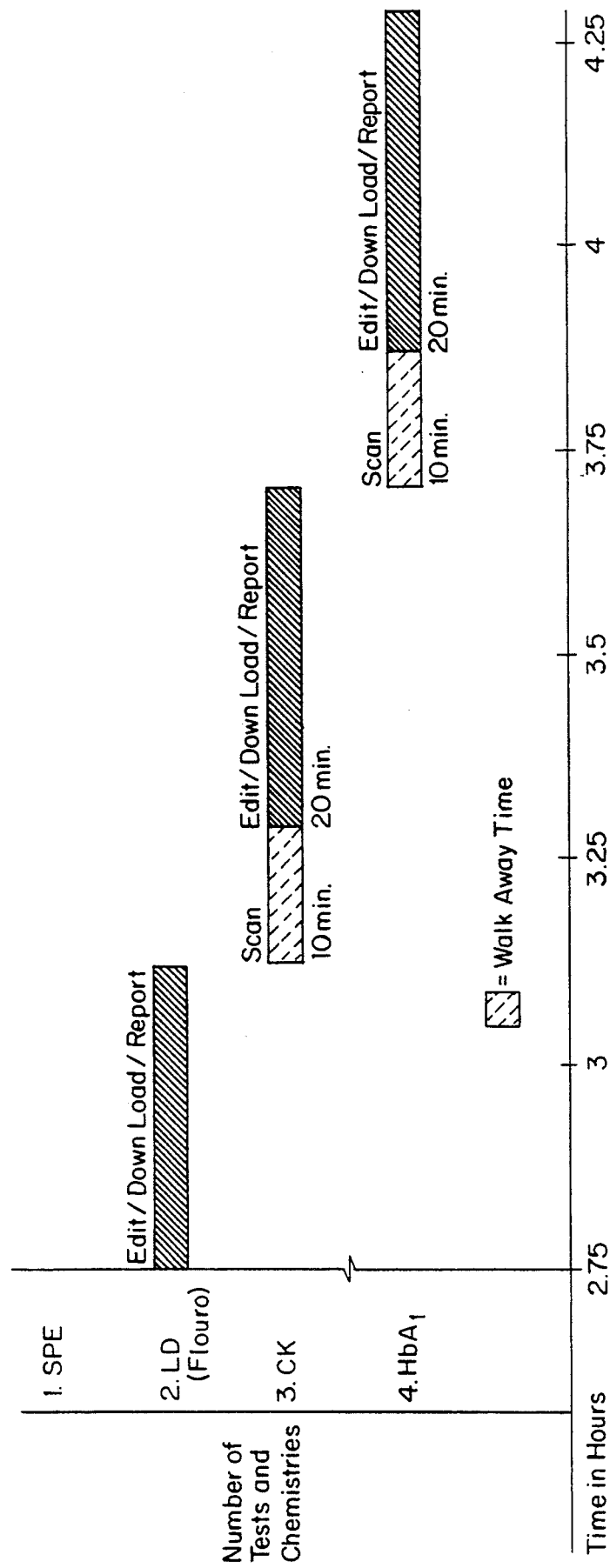
Figure 4A:
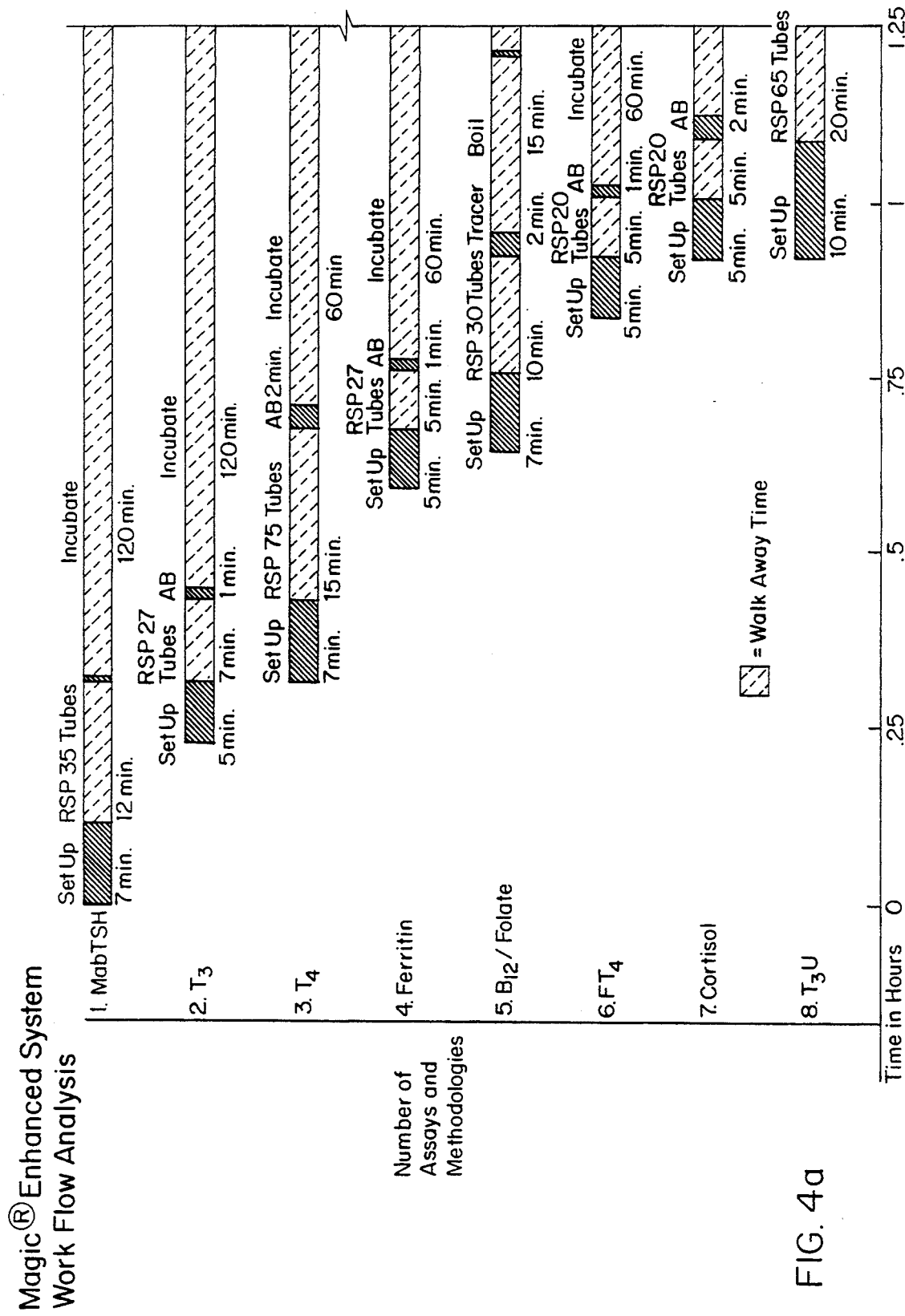
Figure 4B:
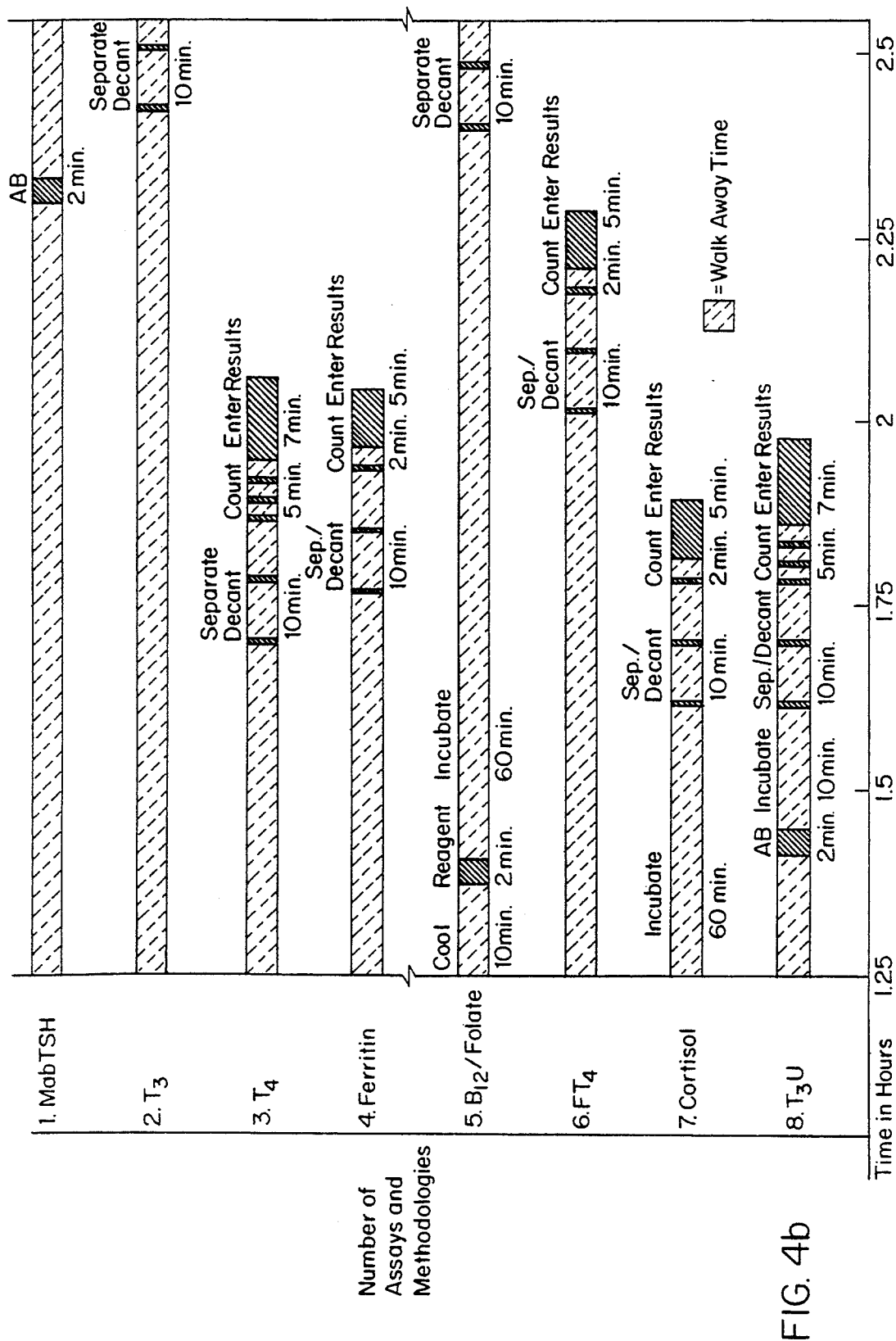
Figure 4C:
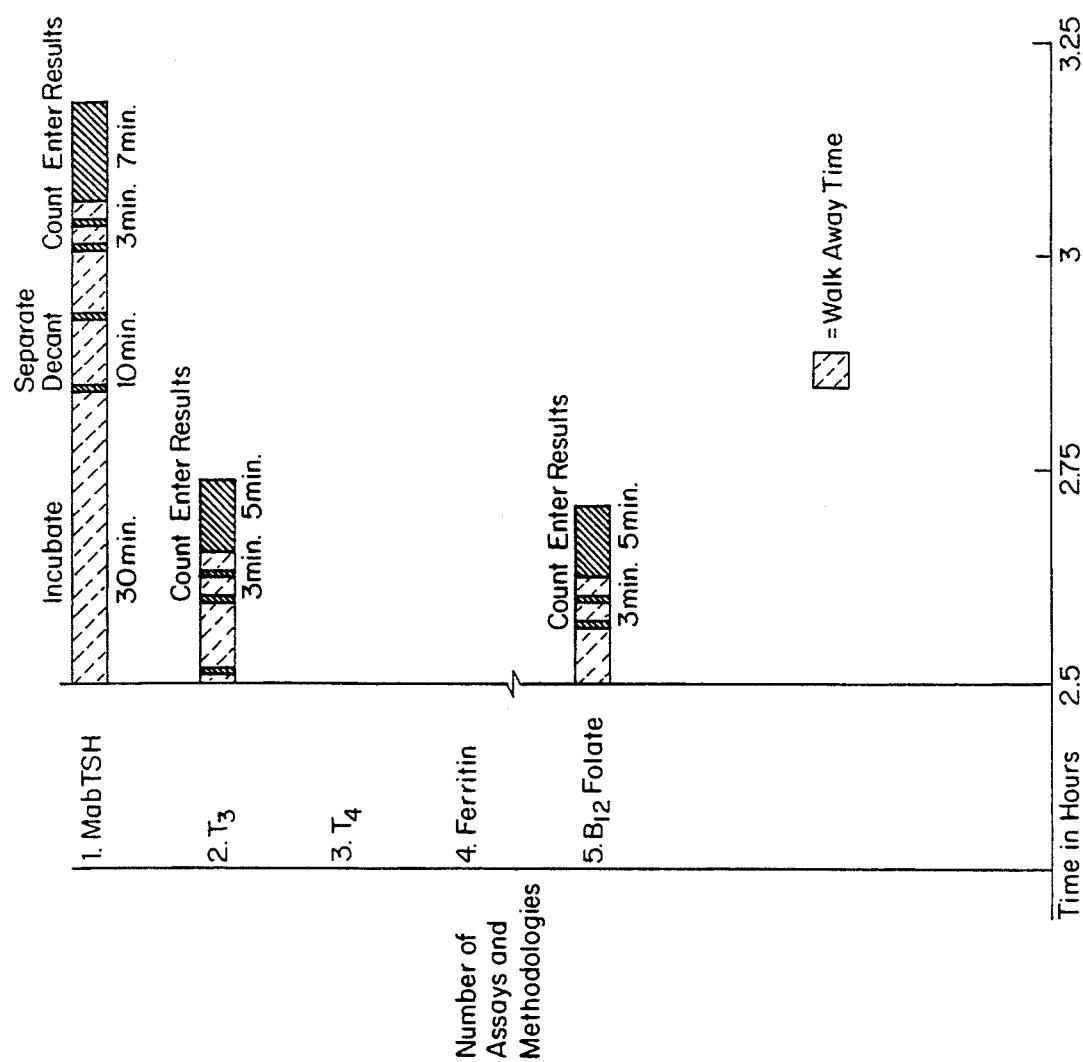
Figure 5A:
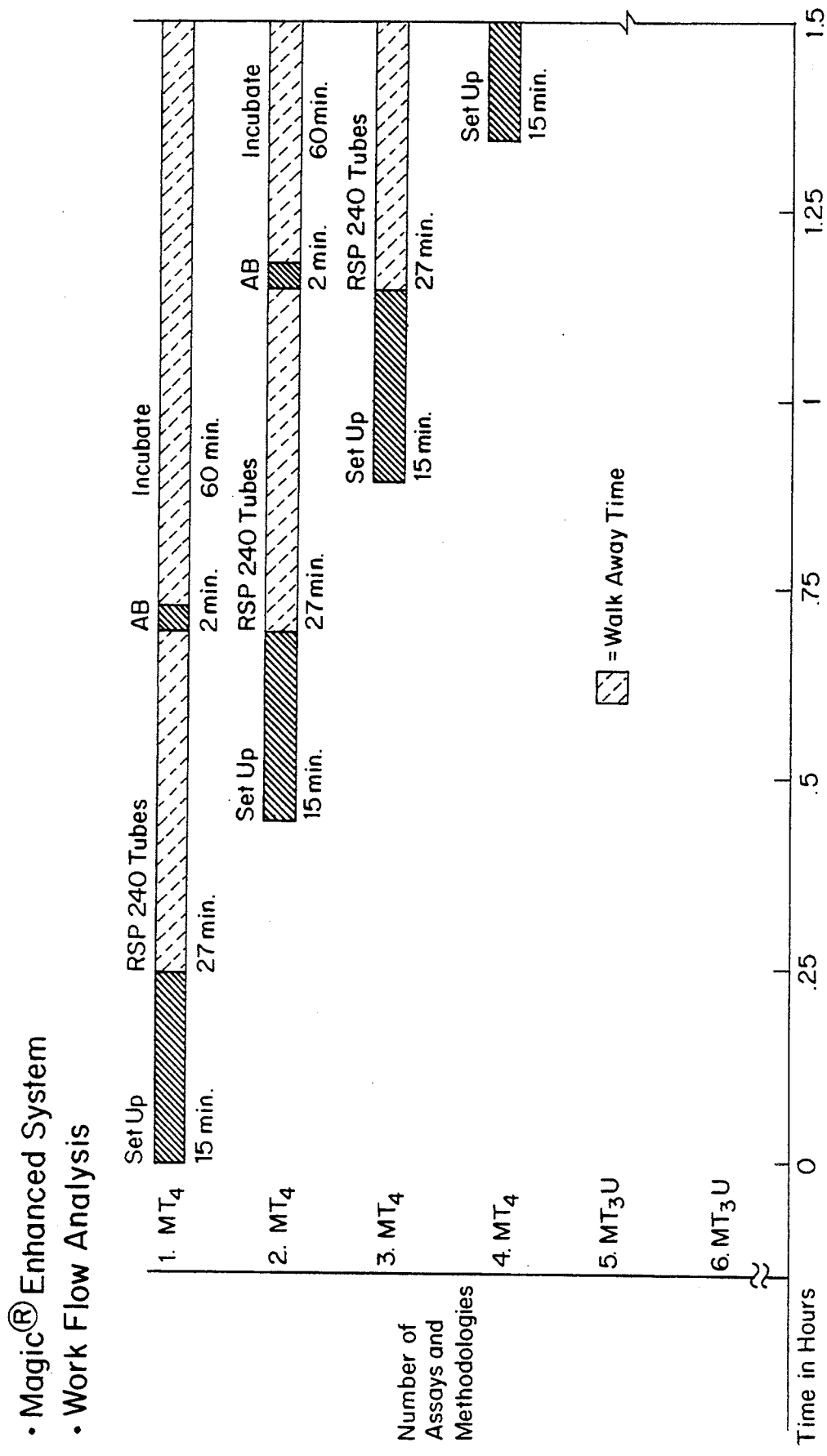
Figure 5B:
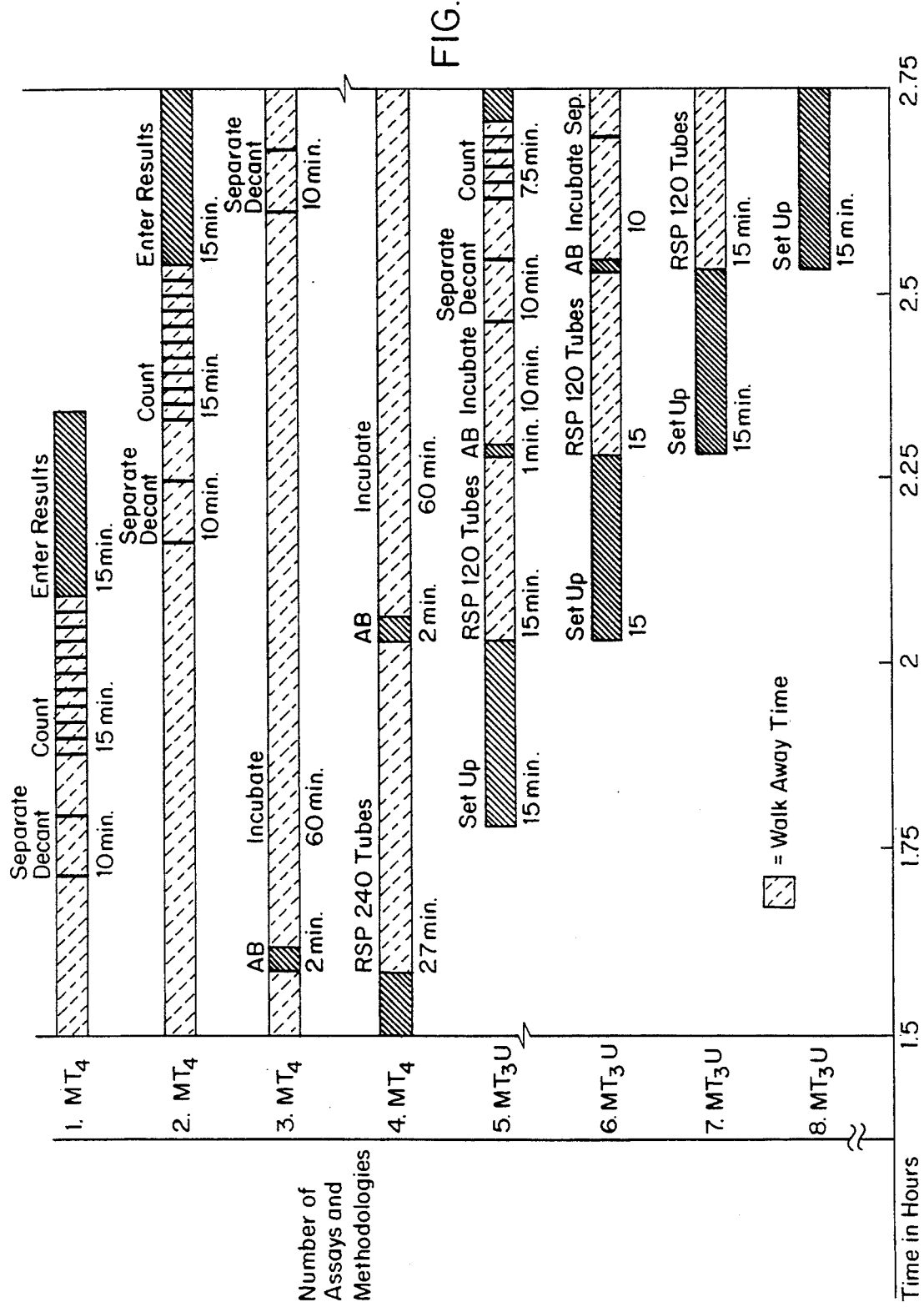
Figure 5C:
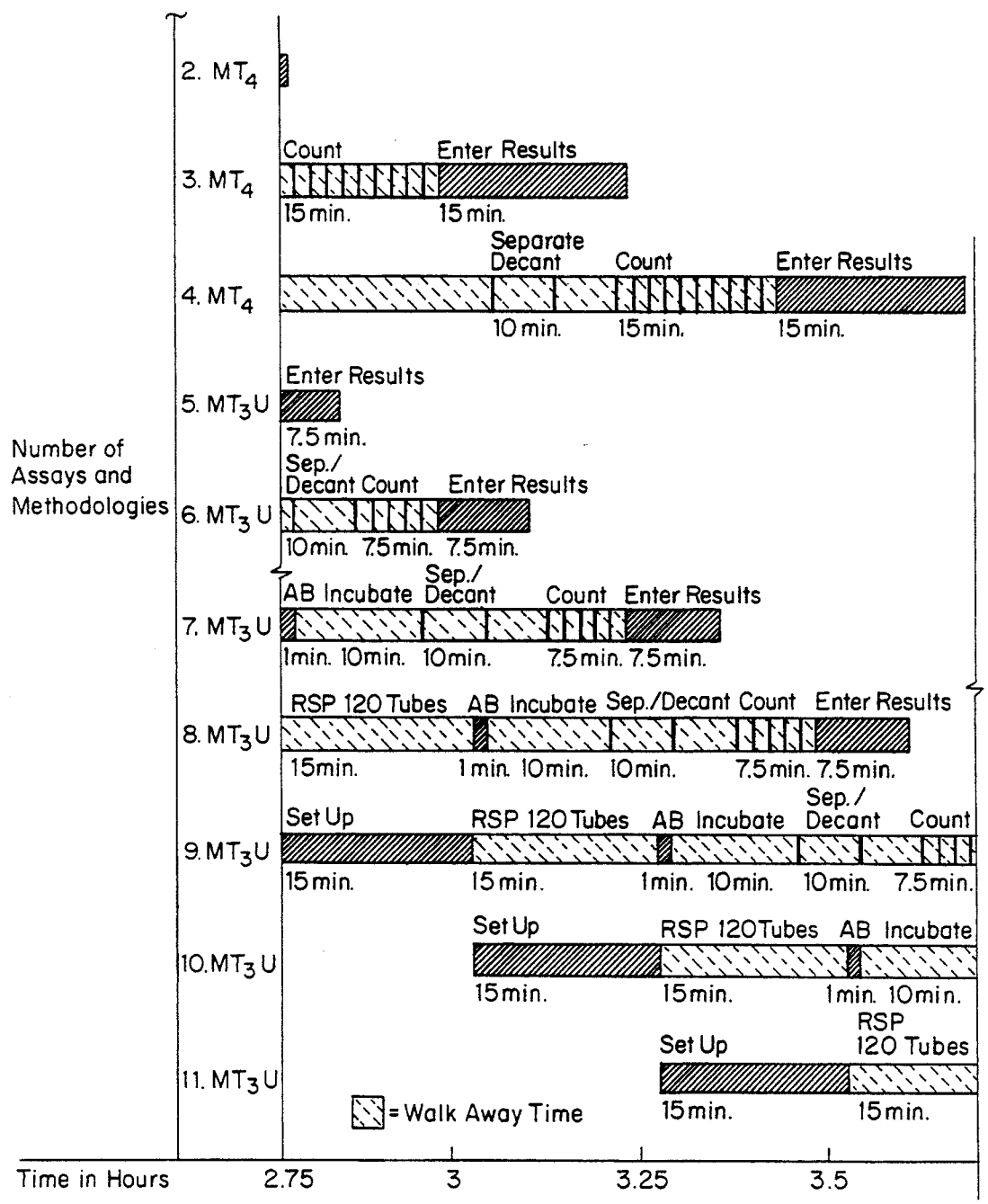
Figure 5D:
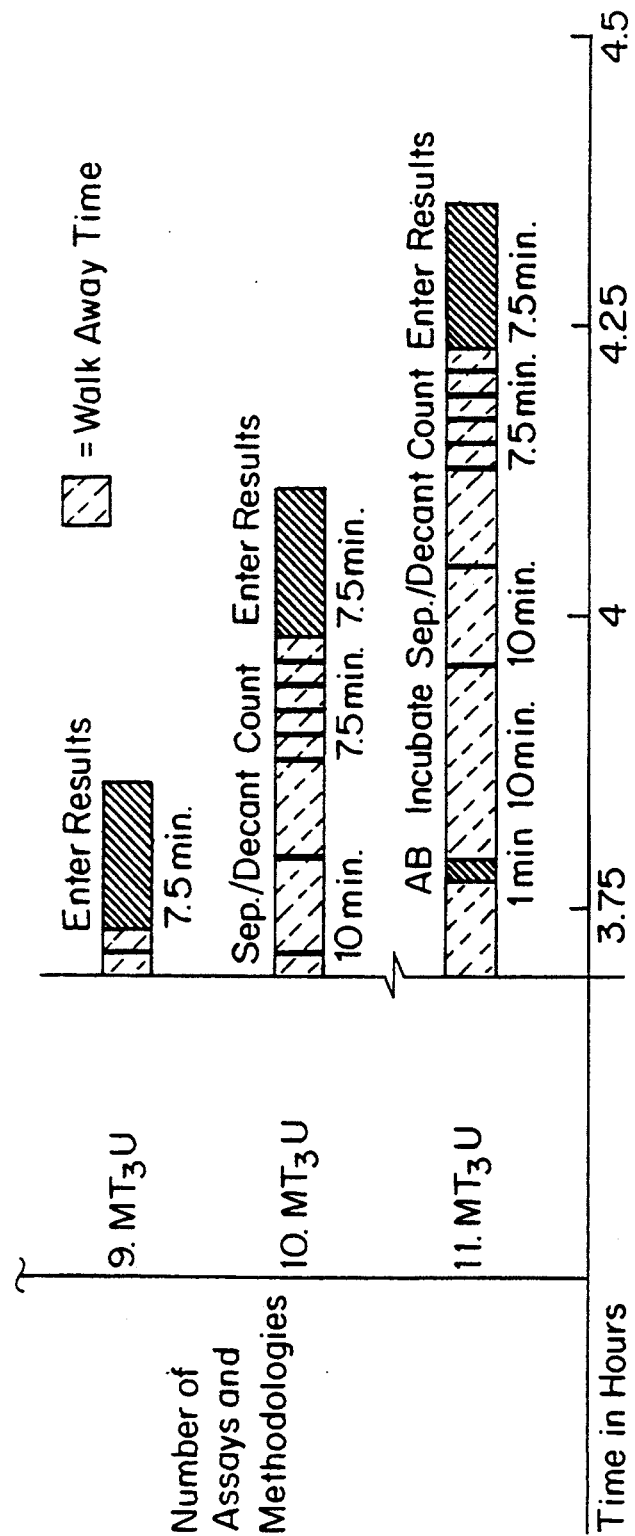
Figure 6A:
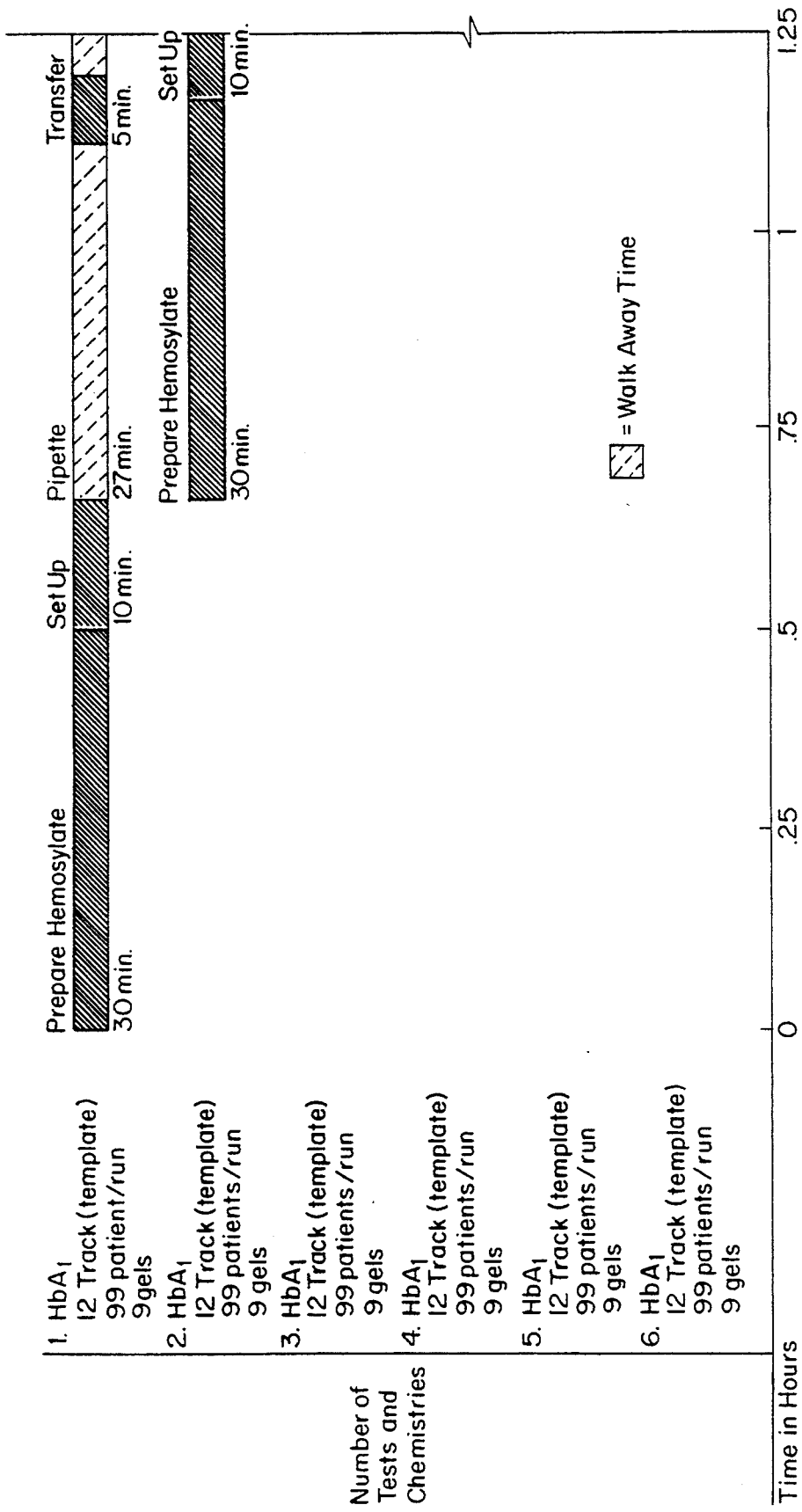
FIGS. 6a–6g are work-flow analysis diagrams of the system as integrated in a large-sized reference laboratory using one (1) technician.
Figure 6B:
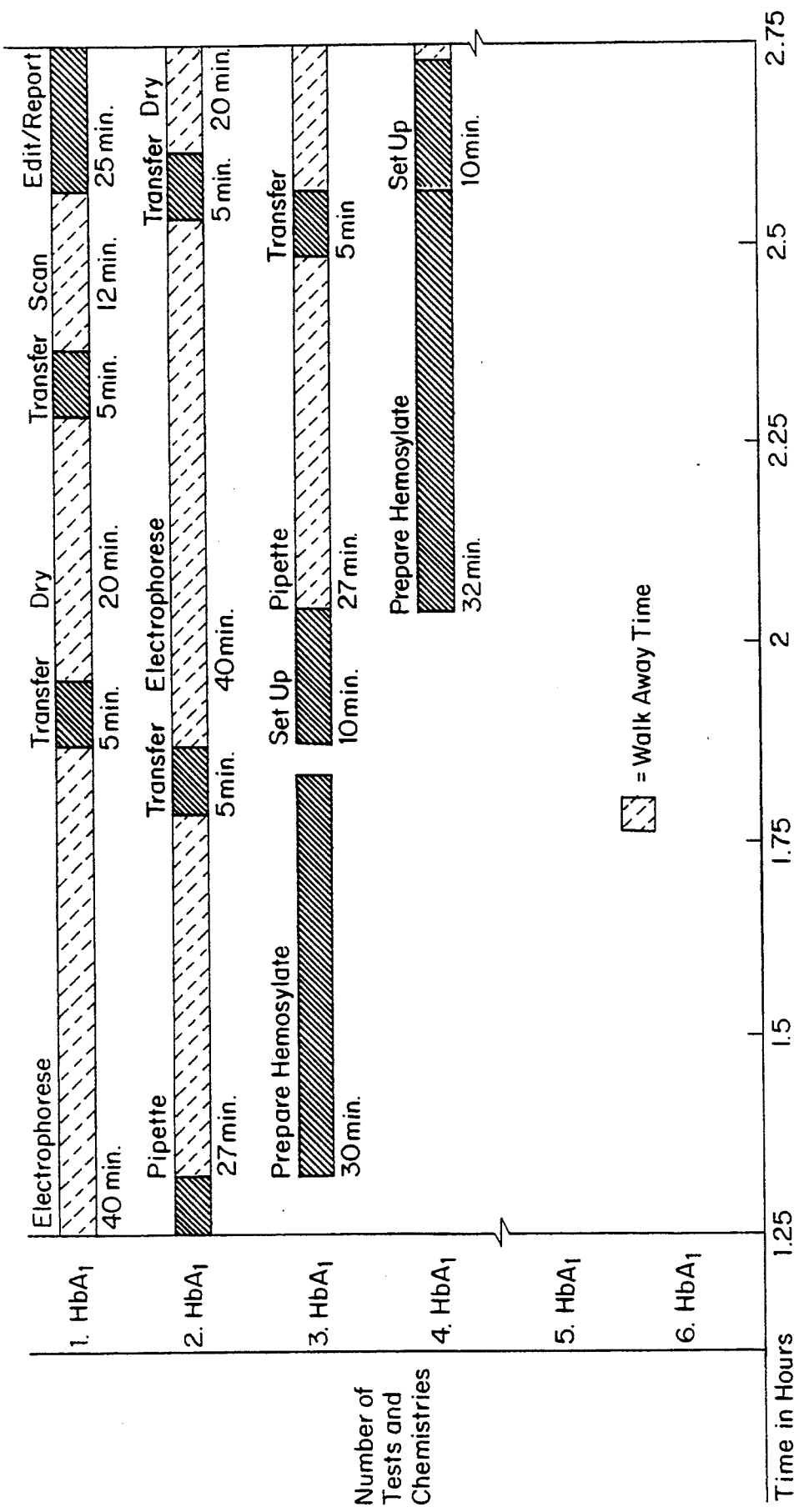
Figure 6C:
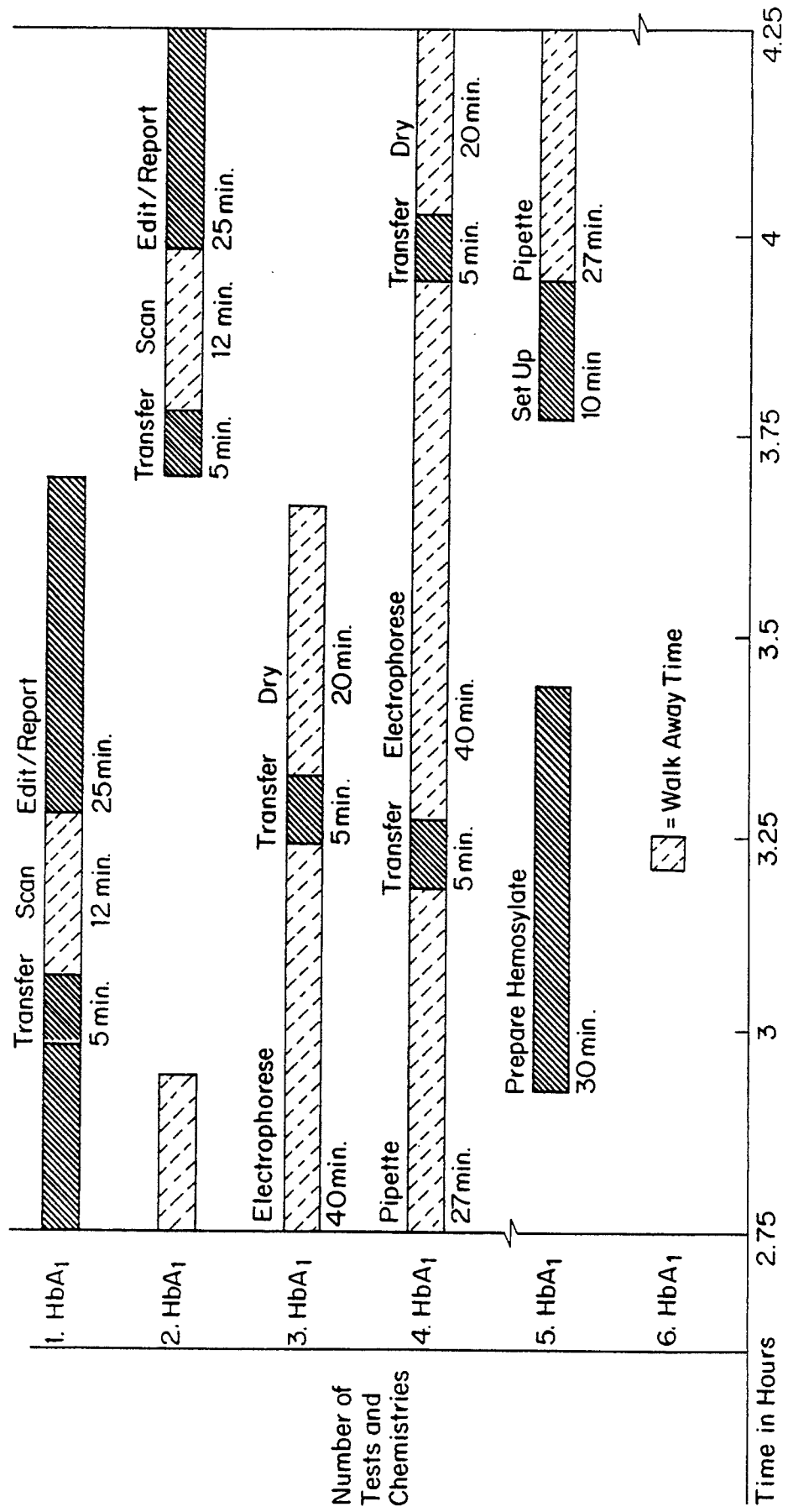
Figure 6D:
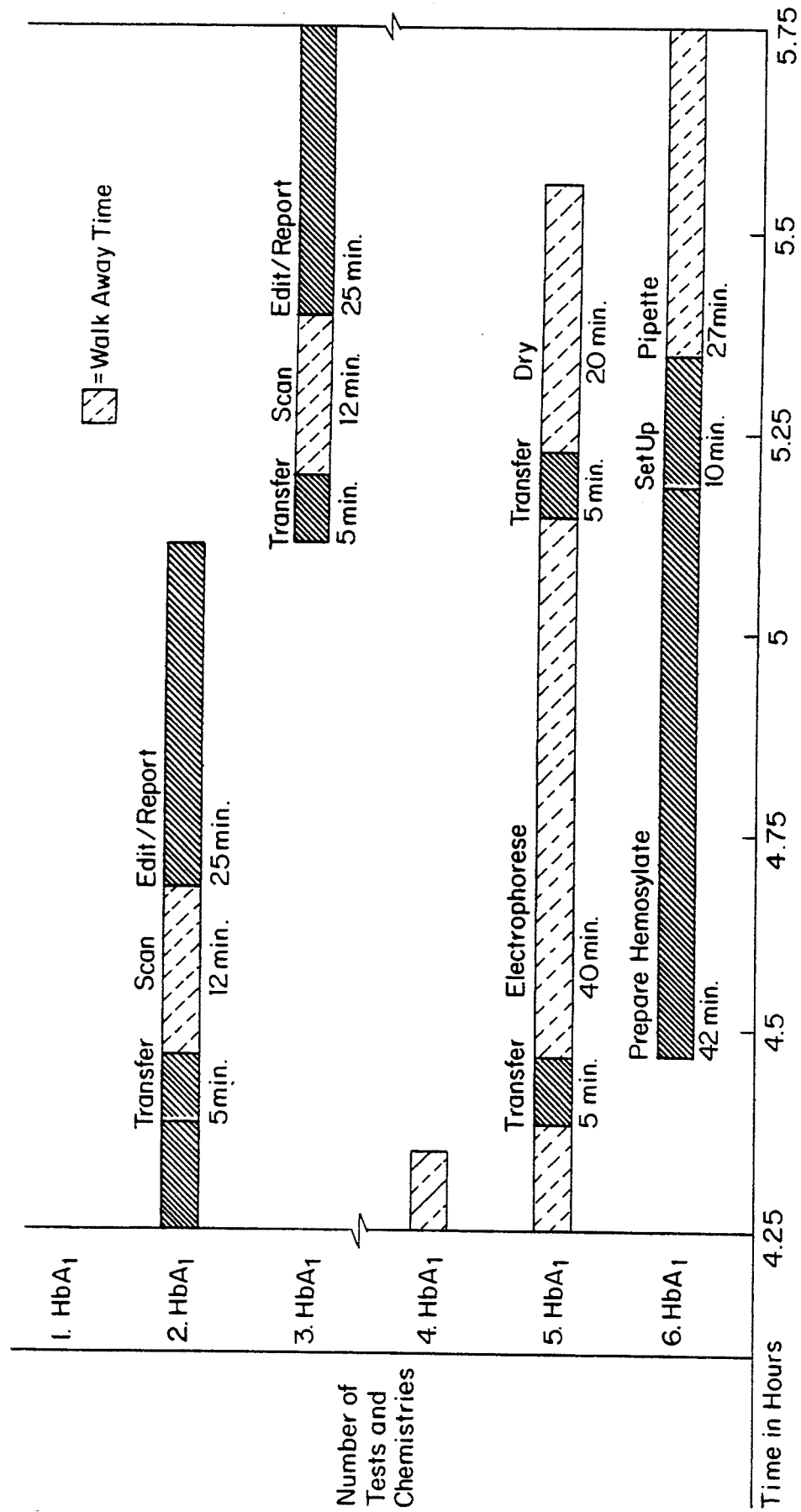
Figure 6E:
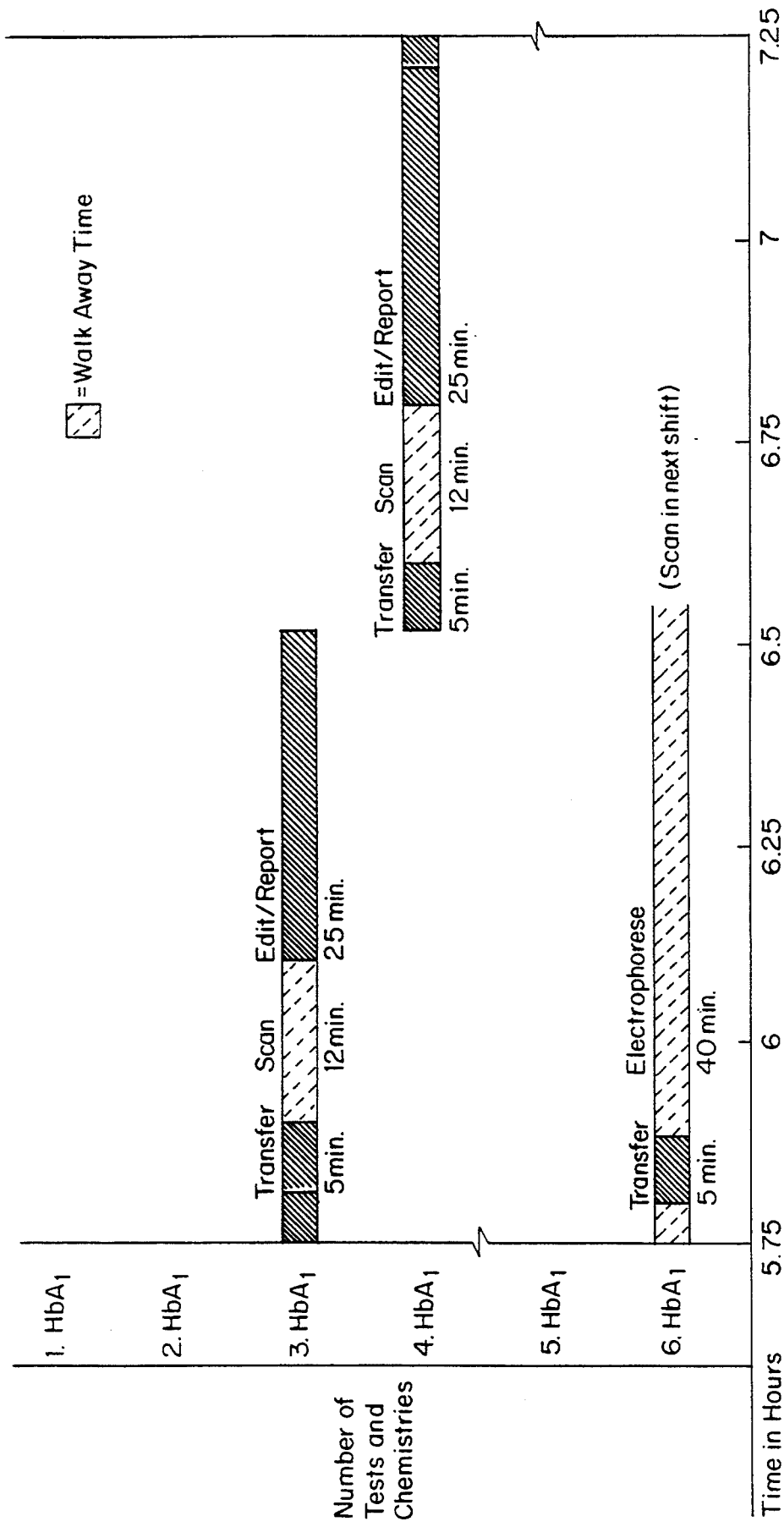
Figure 6F:
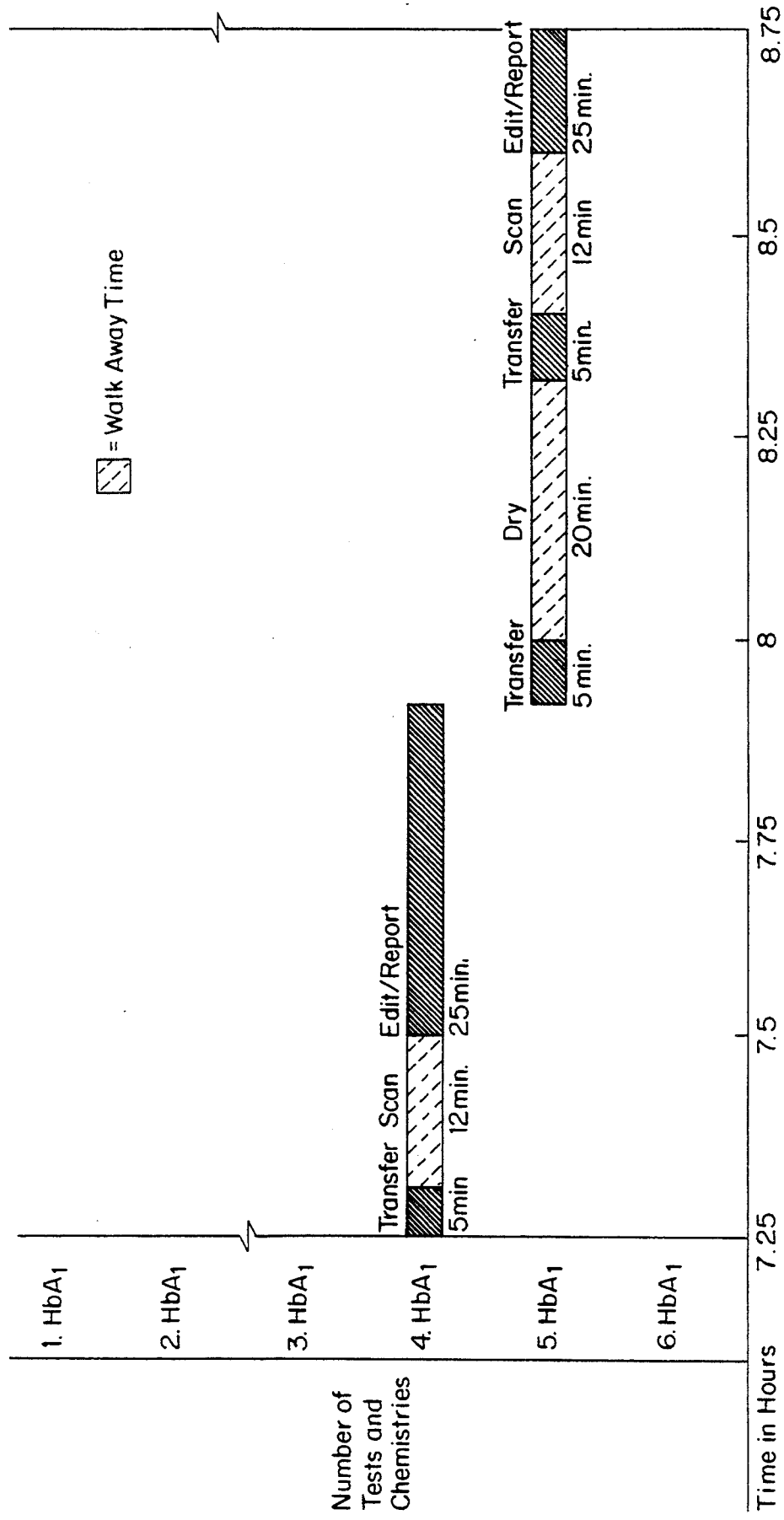
Figure 6G:
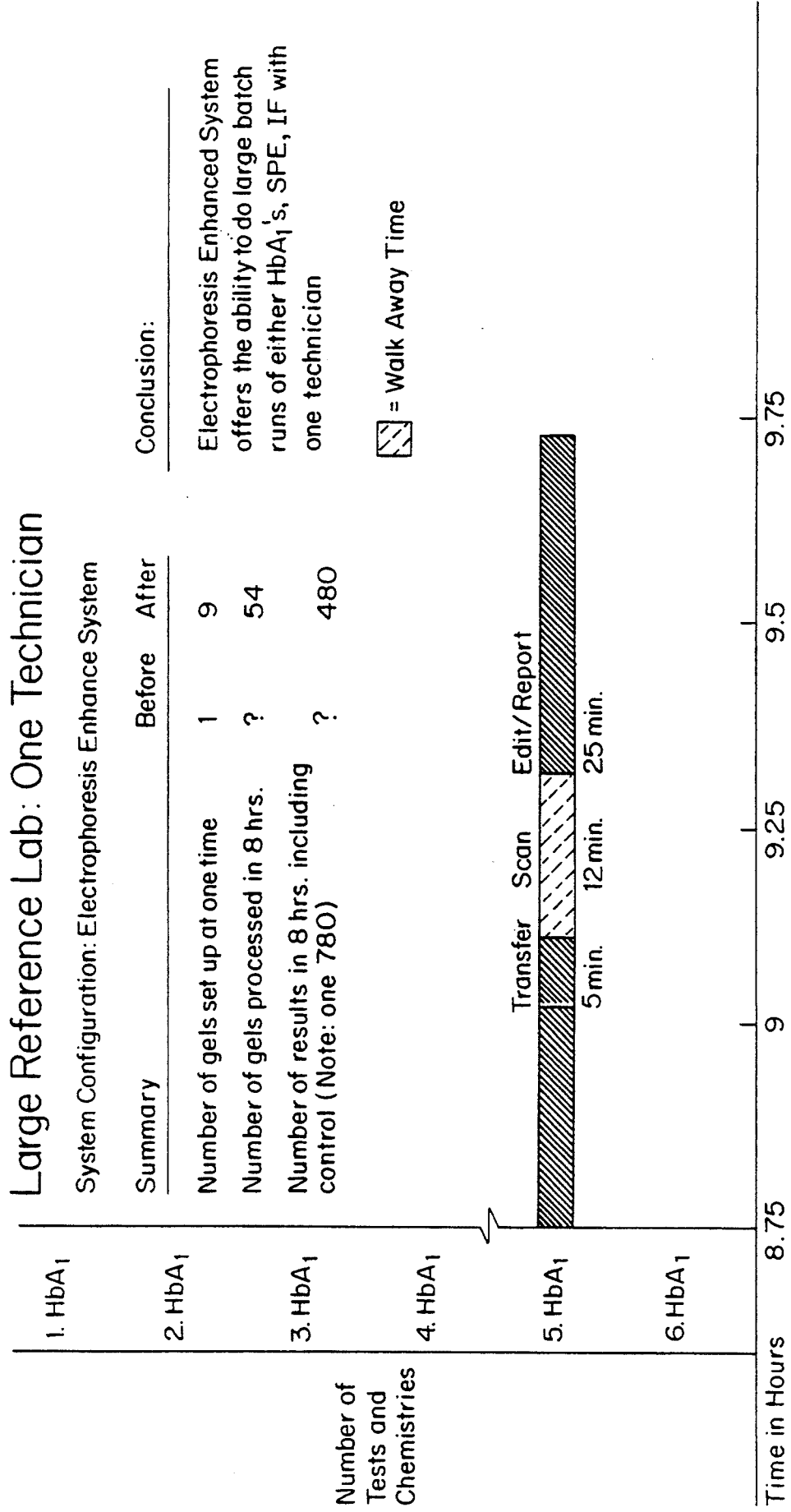

Referring to FIG. 1, the system includes a controller (10) which comprises a memory unit (12) having software for selection of a plurality of immunoassay and electrophoresis protocols. Each program includes test rack and reaction medium layout and format instructions for the robotic sample transfer device which comprise specific speed, cutoffs, washes, air gaps, sample application, and reagent addition restrictions, if applicable, as required for said protocol in order to achieve validated test results for diagnostic use. The programs further provide the robotic sample handling device layout, assay configuration, reagent configuration, pipetting matrix, liquid handling, parameters, and display screen instructions to the system user. The programs are provided in the microfische appendix.

The immunoassay protocols comprise one or more formats of the following assays: Thyroid Stimulating Hormone; T4; Free T4; T3, Free T3; T3 uptake; $B_{12}$/Folate; Ferritin; Human Chorionic Gonadotropic Hormone; Luteinizing Hormone; Follicle Stimulating Hormone; Prolactin; Estradiol; Progesterone; Digoxin; Cortisol; Insulin; Parathyroid Hormone; Aldosterone; CKMB; and T uptake and Chlamydia. The number of formats available to perform an assay in the present system relates to the number of test samples to be processed and/or the source or nature of the assay reagents. The source of the reagents utilized by the system may be from various commercial vendors, such that the format of initiating the test reaction may vary. The time necessary for the kinetic type test reaction(s) to reach equilibrium may also vary. Similarly, the nature of the assay reagents may differ between commercial suppliers. For example, the chemical or physical nature of the reagents may cause the reaction mixture of the test sample and reagent to generate a reaction product which is only detectable by a specific device. Reaction products or detection molecules known in the art for immunoassays include radioactive, luminescent, or fluorescent materials, enzymes which create luminescent, fluorescent or colorometric products, and others.

The preferred immunoassay formats of the present invention incorporate the use of reagents and devices of the Magic ® and Magic ® Lite assay system (Ciba Corning Diagnostics Corp.). The Magic ® and Magic ® Lite assay system reagents were validated for each protocol noted above. A validated protocol is defined as one where test results obtained are diagnostically the same whether the test sample and reagent transfer steps were performed manually or when using the system. Test result validation is a function of the program specific to each protocol. Further testing was performed to check for end of run drift by examining results of control test samples ordered at the beginning and at the end of the protocol. Sample carry-over was also analyzed by testing high control standards followed by a zero control standard, both manually, and using the robotic sample transfer device, and comparing inter and intra assay replicates.

The number of test samples that may be assayed per selected immunoassay protocol is limited by a rule of kinetics which manifests itself when kinetic-type protocols are performed with a robotic transfer device. The rule as applied to the system mandates that the total time required to add the kinetic reagent by the device can not be longer than ten percent of the total incubation time for the selected protocol. The failure to comply with this rule would cause the generation of inaccurate test results, because of variations in the time that a test reaction reaches equilibrium after the kinetic reagent is added, and thereby prevent the use of the test results for diagnostic purposes. The computer programs for the effected immunoassay protocols of the test system incorporate the application of this rule, such that the number of test samples that are ordered in the test racks will be limited in proportion to the incubation time of the protocol.

It is understood that the format of a protocol may be modified to alter the kinetics of the test reaction and thereby change the incubation time. The kinetic reagent may alternatively be added manually after the reaction medium(s) is removed from the deck. If changes in the format are made, then further validation studies would be necessary to compare manual and semi-automated processing.

The electrophoresis protocols of the system comprise the following assays: Creatine Kinase Isoenzymes; Lactate Dehydrogenase; Serum Protein Electrophoresis; Hemoglobin $A_1$; Alkaline Phosphotase; Lipoprotein; High Density Lipoprotein; Immunofixation; Immunoelectrophoresis; High Resolution Serum Protein; Hemoglobin Alkaline; and Hemoglobin Citrate. In the preferred embodiment, protocol specific agarose gels (Ciba Corning Diagnostics Corp.) are utilized. The electrophoresis protocols were validated, in that a protocol performed by the system yielded diagnostically the same test results when the protocols were performed manually. The electrophoresis protocols require that the volume of test sample applied to a gel be 1 ul. Derivations from this volume and an unlevel deck, as described below, will have a negative impact on the test results, such that the results are not diagnostically accurate. The precise sample application of electrophoresis test samples eliminates the most labor intensive and technique-sensitive part of the protocol.

In the preferred embodiment the memory unit has sufficient capacity to add more protocols to conform to the needs of the user laboratory and to accommodate newly developed protocols. The addition of more protocols to the system would require validation studies as noted above, before the test results of said protocols could be used for diagnostic purposes.

The controller further includes means for selecting an immunoassay or electrophoresis protocol from the memory unit. In the preferred embodiment the means for selecting a protocol comprises a keyboard (14). The keyboard may be an integral unit of the controller or be a separate component having a communication linkage to the controller. The choice of protocol selection is based on the work-flow demand of the user laboratory. The daily work-flow demand of the laboratory should be further evaluated to sequence the order of protocols beginning with the protocol that has the longest incubation or electrophorese time. The advantage of such protocol sequencing is to enable the system to time-effectively perform the protocols required by the work-flow analysis with the available FTE(s).

The controller also includes a means for entering the number of test samples to be assayed for the selected protocol. In the preferred embodiment the means for entering the number of test samples is a keyboard. The keyboard utilized for this function may be the same keyboard which is utilized to select the protocol as noted above. It is understood that further identifying characteristics may be entered to further define the test samples to be assayed; such characteristics may include an assigned test sample number or in the case of patient test samples, the patient name or a patient identification number.

A display screen (16) is another component of the controller. The display screen, following entry of one or more keystrokes on the keyboard, will project a sequence order for the placement of test sample containers (24) in one or more test rack(s) (22). The number of test racks used being dependent on the number of test samples entered and the protocol. The test sample containers have deposited therein a sufficient volume of test sample (not shown) to perform the selected protocol. It is required that the display screen be in communication with the memory unit.

The controller in the preferred embodiment is a computer (IBM PC 50, International Business Machines). Other commercial computers may be utilized as a controller provided the memory unit thereof is sufficient for storing and running the programs necessary to practice the invention. It is understood that the application of the system to various use settings may require that the programs be entered into a mainframe computer located on or off-site of the system user. A keyboard and display screen, each having a communication linkage to the mainframe would be located in the laboratory.

The robotic sample transfer device (20) of the preferred embodiment is a Tecan RSP 5051 and/or 5052 (TECAN HANDELS AG). The robotic transfer device comprises a planar deck (26), having defined coordinates, such that transfer means, in the form of one or more robotic arm(s) (28) transfer a volume of test sample and one or more reagents to and from various positions of the work surface. In the preferred embodiment the deck for immunoassay testing is adapted to be mounted onto the electrophoresis deck when an immunoassay protocol is selected. It is understood that if a system user does not perform electrophoresis testing a robotic transfer device may be provided without the electrophoresis deck. A system designed to perform only electrophoresis testing may be provided for a system user. The robotic arm(s) include an aspiration and sample delivery conduit.

In the preferred embodiment, the deck is adapted to have one or more test sample rack(s) (22) and one or more reaction mediums (23) mounted thereon in defined positions. A reaction medium is defined as a site for interacting test sample and one or more reagents to initiate a test reaction. In the immunoassay protocols the reaction medium is a test tube. In the electrophoresis protocols, the reaction medium is an electrophoresis gel, upon which one or more test samples may be deposited, the volume of the test sample applied to the gel being 1 ul. The accuracy of the 1 ul. sample volume was verified by applying a serum sample containing a known amount of an isotope ($^{125}I$) onto a gel; and then the site of the test sample application on the gel was removed and counted by a gamma counter. The robotic sample applicator successfully manages the most labor-intensive step of the protocols.

During the period of time in which the robotic sample transfer device is transferring volumes of test sample and in the immunoassay protocols transferring reagents the FTE is preparing test samples and reagents for the next protocol to be run on the system, or other functions in the laboratory.

It is a further embodiment of the present invention that the electrophoresis deck be adjustable to a tolerance level of 0.01 mm. This adjustment capacity coupled with the accurate and precise transfer of 1 ul. of test sample onto the gel provide the means for generating test results that are diagnostically accurate.

Following the transfer of test sample and one or more reagents to the reaction medium, the test racks and reaction medium are removed from the deck to allow sample transfer for subsequent protocols. The removed test mediums are processed in accordance with the assay methodology as described for the protocol to effect a detectable reaction product. In the electrophoresis protocols, for example, the gels are electrophoresed and stained. The assay methodology for processing the removed test mediums is generally provided in written form (product insert) for each protocol. The assay methodology may, for example, be incorporated in a package insert of a reagent kit, which is specific for a protocol.

The FTE continues the described work-flow until all the test samples have been processed. Referring to the case studies below will provide and illustration of work-flow diagrams.

One or more detection devices (30) are required to determine a test result for each reaction product of the test samples analyzed. Various detection devices are known in the art for determining test results for immunoassay and electrophoresis protocols. In the described system a MLA instrument (Ciba Corning Diagnostics Corp.) which detects chemiluminescent reactions is utilized for determining test results for some of the immunoassay protocols. Other immunoassay protocols, as noted above, or as may be added to the system, incorporate the use of radioisotopes and thereby require the use of a gamma or beta counter which is calibrated for a specific radioisotope to determine test results. Alternatively, a fluorometer/densitometer, Model 780, (Ciba Corning Diagnostics Corp.) is utilized for determining test results for the electrophoresis protocols.

Test results from the protocols may be reported on any number or form of media known in the art. Remote data processing systems (Ciba Corning Diagnostics Corp.) are available for reporting of results and data management for electrophoresis. The reporting of results and data management functions vary between laboratories; and it is not required that a laboratory modify these functions when the described system is integrated into the laboratory.

The invention is further demonstrated by the following examples which represent case studies of the application of the system in various laboratories. The examples are intended to illustrate and not to limit the invention.

EXAMPLE 1

Referring to FIGS. 2a–2d, the system was implemented in a small clinic which sought to semi-automate their immunoassay testing. The clinic's primary objective was to effect a time savings in both turn around time for reporting test results following receipt of test samples and run time for the selected protocol.

FIGS. 2a–2d represent work-flow analysis diagrams which illustrate the sequence for performing five successive assays for four selected immunoassay protocols with the system. The five assays were completed in approximately three and one-half hours, and generated results for three hundred and forty-five test samples. The test samples included control samples, blank samples, standard samples, and patient samples.

The legend of FIG. 2d provides a comparison of manual (Before implementation) and semi-automated (After implementation) processing of the same number of test samples and protocols. The "After" data reflect the time savings achieved and a reduction in FTE necessary to process the test samples.

Financial analysis is also provided in the legend. The analysis is based on an assumed labor cost for a FTE per year and a revenue generation estimate that one FTE can generate in a month. The annual labor cost saved and the increase in annual opportunity value denotes the efficiency of the system as applied to a small clinic.

EXAMPLE 2

Referring to FIGS. 3a–3d, the system was implemented in a medium to large hospital which provides a range of daily electrophoresis testing. The hospital sought to integrate a flexible electrophoresis system to accommodate their daily electrophoresis work-flow.

FIGS. 3a–3d represent work-flow analysis diagrams which illustrate the sequence for performing four successive assays for four selected electrophoresis protocols with the system. The four assays were completed in approximately four and one-half hours with one technician. One hundred and fifty-two test samples, including controls, were processed by the system. The system's robotic sample transfer device applied test samples to the gels and thereby eliminates the most labor intensive and technique-sensitive part of the protocol. The automated sample transfer provides the technician with walk away time which can be optimally utilized to set up subsequent samples for processing.

The legend of FIG. 3d provides a comparison of manual (Before implementation) and semi-automated (After implementation) processing of the test samples. The elimination of the sample application after integration of the system reduced the pipetting time during the four hours by approximately one hour.

EXAMPLE 3

Referring to FIGS. 4a–4d, the system was implemented in a large hospital (600 beds) which sought to reduce their immunoassay run time and to expand the number of test protocols that could be processed by the hospital laboratory. A review of the laboratory's daily work-flow was initially performed to determine the level of efficiency that would be achieved on integration of the system.

FIGS. 4a–4d represent work-flow analysis diagrams which illustrate the sequence for performing a total of eight successive assays for eight selected immunoassay protocols with the system. The eight assays were completed in approximately three and one-half hours, and generated results for two hundred and ninety-nine test samples. The test samples included control samples, blank samples, and patient samples.

The legend of FIG. 4d provides a comparison of manual (Before implementation) and semi-automated (After implementation) processing of the same number of test samples and selected protocols. The "After" data reflect the time savings achieved in total run time and in the number of FTE(s) required to process the test samples. Turn around time was improved by approximately four and one-half hours and labor was reduced by approximately forty-two percent.

A financial analysis is also provided in the legend. The analysis is based on an assumed labor cost for a FTE per year, and a revenue generation estimate the one FTE can generate in a month. The annual labor cost saved and the increase in annual opportunity value denote the efficiency of the system as applied to a large hospital. The noted efficiency provides the hospital with the option to expand the number of test protocols performed by its laboratory.

EXAMPLE 4

Referring to FIGS. 5a–5e, the system was implemented in a large reference laboratory. The laboratory's primary objective was to effect a reduction of FTEs and to improve turn around time for reporting test results following receipt of test samples.

FIGS. 5a–5e represent work-flow analysis diagrams which illustrate the sequence for performing a total of eleven successive assays for two selected immunoassay protocols with the system. The eleven assays were completed in approximately five hours, and generated test results for one thousand eight hundred test samples. The test samples included control samples, blank samples, standard samples, and patient samples.

The legend of FIG. 5e provides a comparison of manual (Before implementation) and semi-automated (After implementation) processing of the same number of test samples and selected protocols. The "After" data reflect a reduction in the FTE necessary to process the test samples and an improved turn around time. The labor was shown to be reduced by approximately thirty-three percent turn around time was improved by three hours, and run time was reduced by approximately thirty-eight percent.

A financial analysis is also provided in the legend. The analysis is based on an assumed labor cost for a FTE per year and a revenue generation estimate that one FTE can generate in a month. The annual labor cost saved and the increase in annual opportunity value denote the efficiency of the system as applied to a large reference laboratory.

EXAMPLE 5

Referring to FIGS. 6a–6g, the system was implemented in a large reference laboratory which sought to reduce FTE in the performance of electrophoresis testing.

FIGS. 6a–6g represent work-flow analysis diagrams which illustrate the sequence for performing six successive assays for one selected electrophoresis protocol. Five of the six assays were completed in approximately nine and one-half hours; the sixth assay required scanning of the test results during the next shift of labor. A total of four hundred and eighty test samples, including control samples, were processed in eight hours. The test samples were applied to fifty-four gels by one FTE, each gel having twelve tracks for test sample application. The case study shows that the system enables one FTE to perform large batch runs of electrophoresis protocols.

EXAMPLE 6

Referring to FIGS. 7a–7e, the system was implemented in a large reference laboratory which sought to semi-automate batch immunoassay testing. A work-flow analysis was performed to determine the efficiency that could be achieved upon integration of the system.

FIGS. 7a–7e represent a work-flow analysis diagram which illustrates the sequence for performing a total of ten successive of one selected immunoassay protocol with the system. The assays were completed in approximately seven and one-half hours and generated test results for two thousand four hundred test samples. The test samples included control samples, blank samples, standard samples, and patient samples.

Figure 7A:
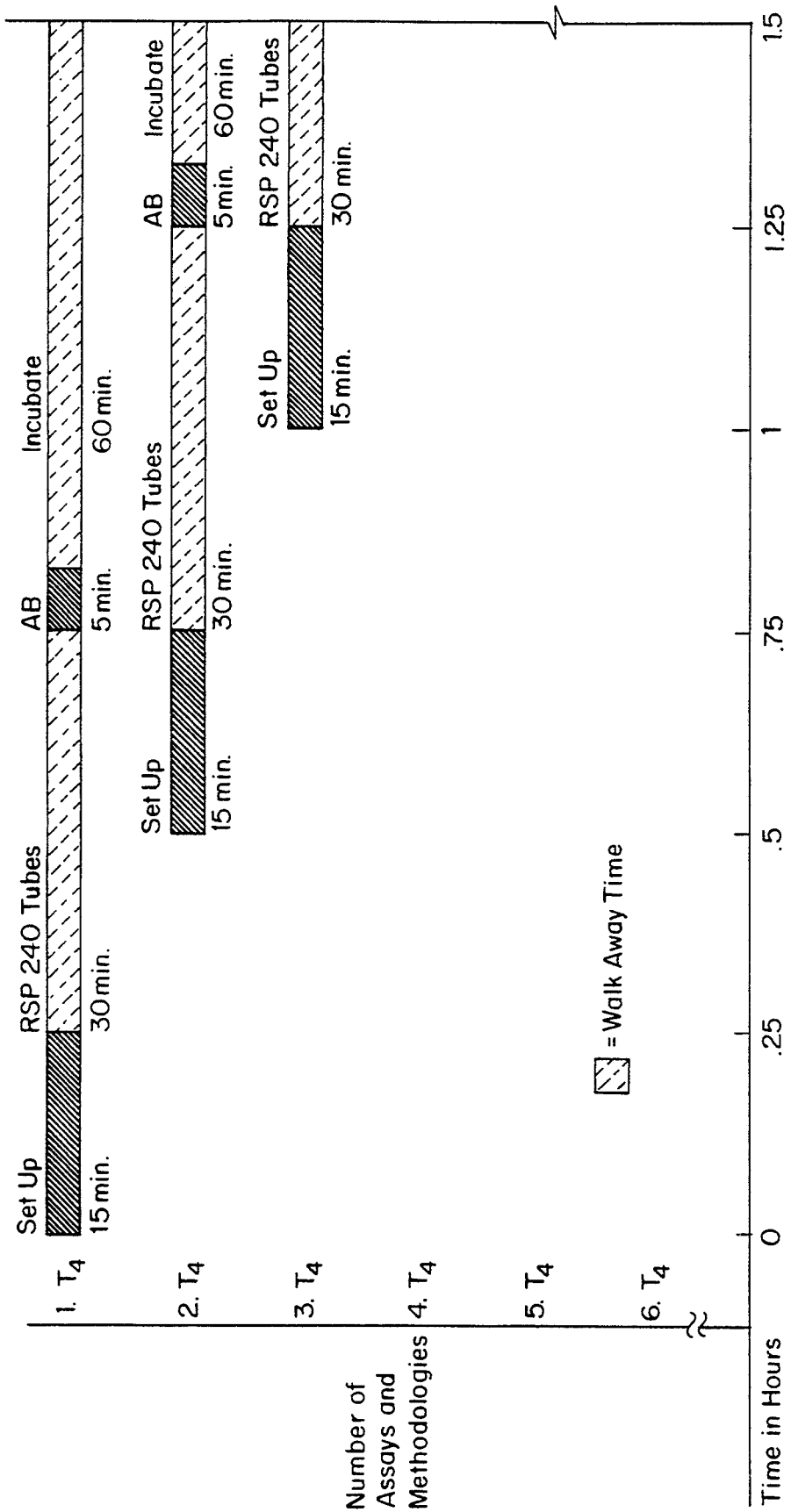
FIGS. 7a–7e are work-flow analysis diagrams of the test system as integrated in a large-sized reference laboratory.
Figure 7B:
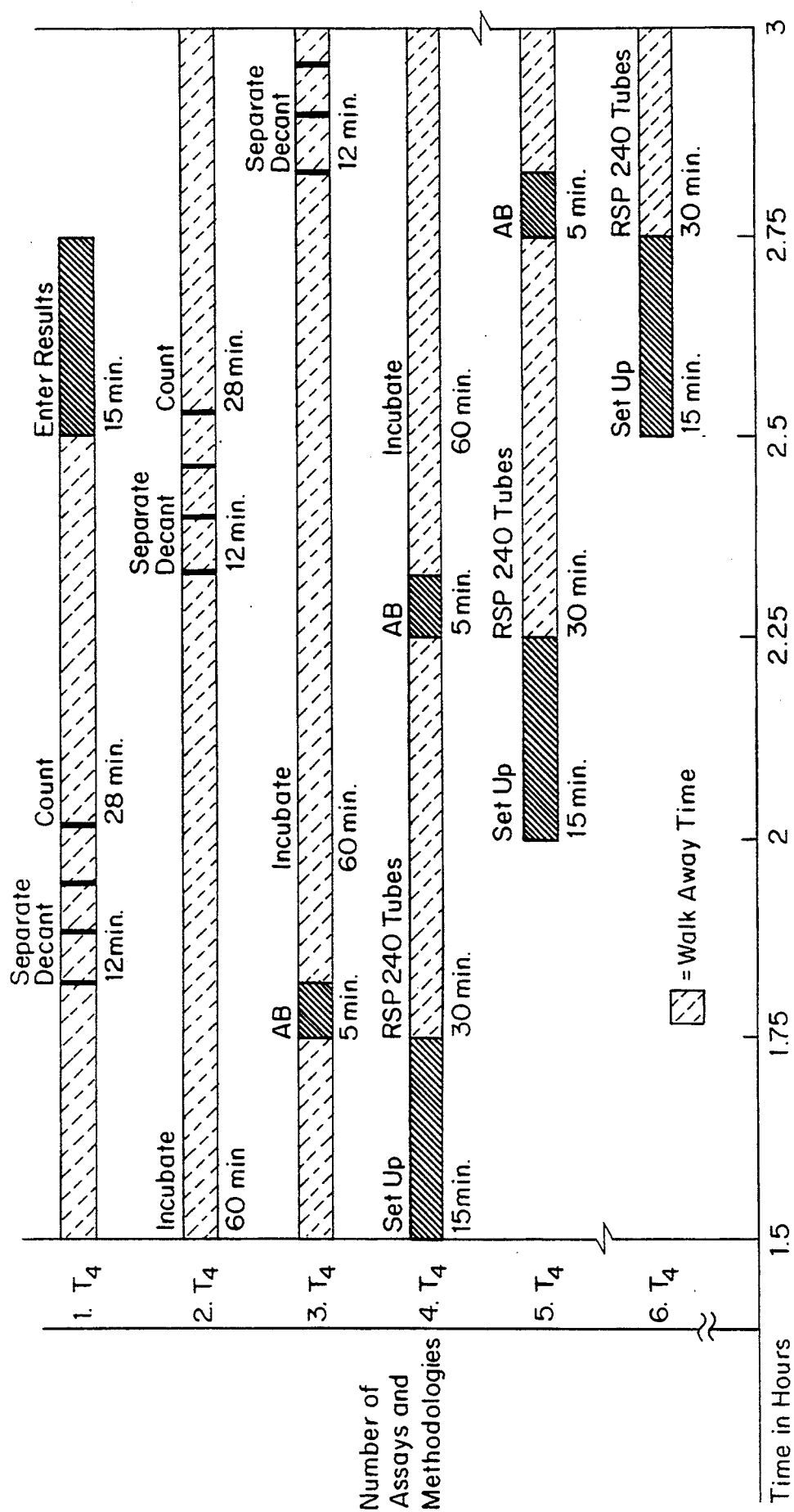
Figure 7C:
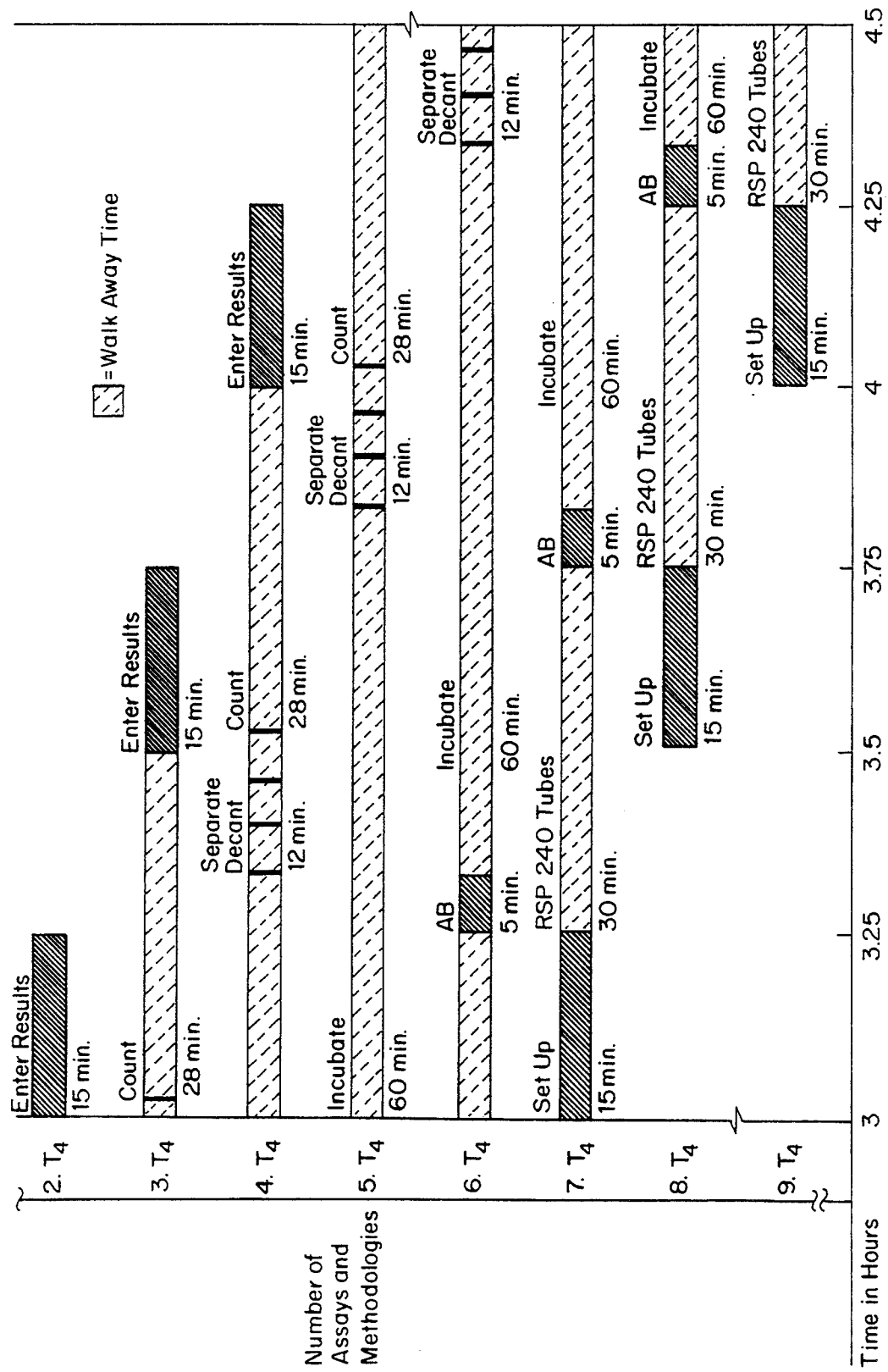
Figure 7D:
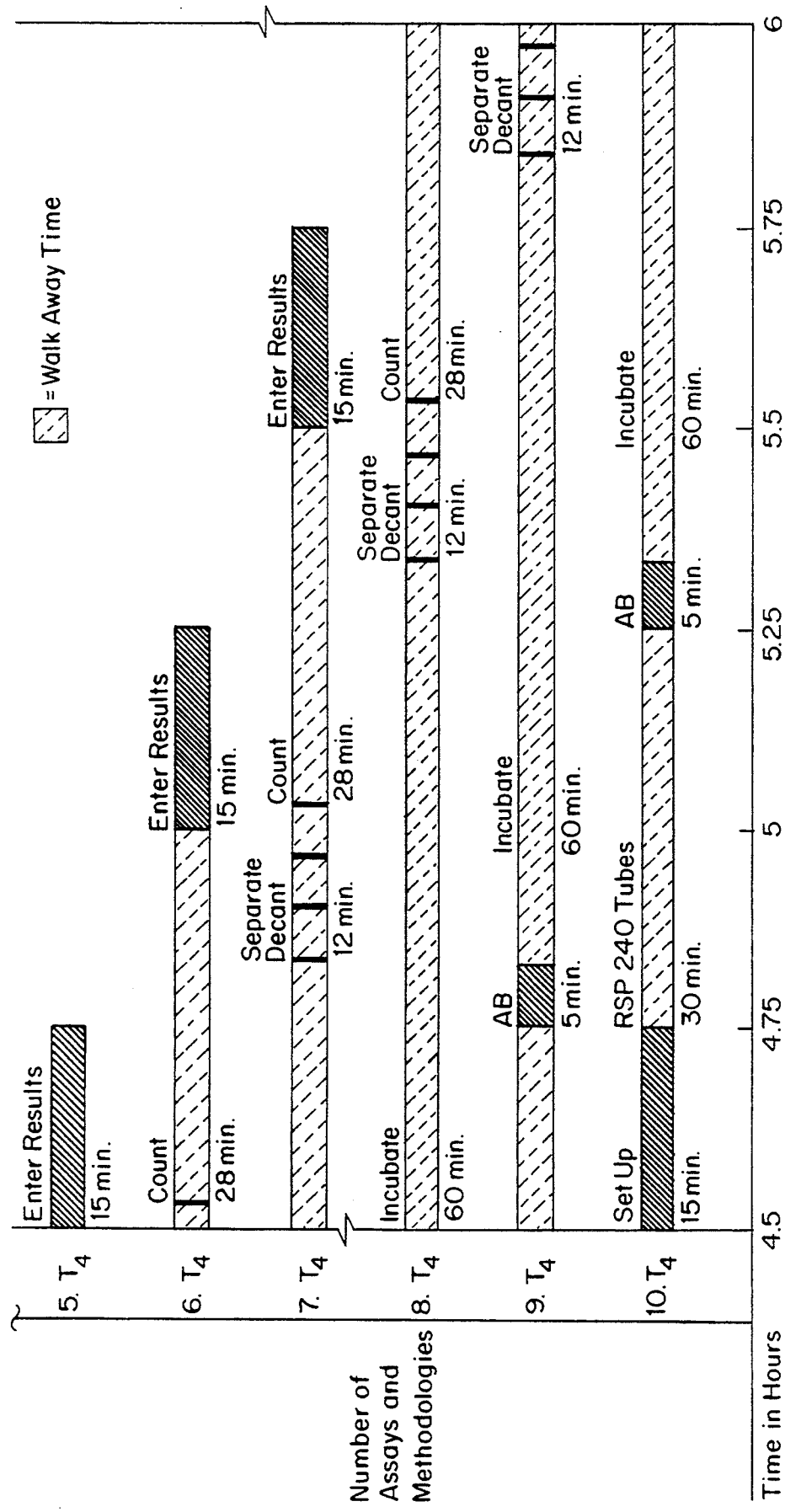
Figure 7E:
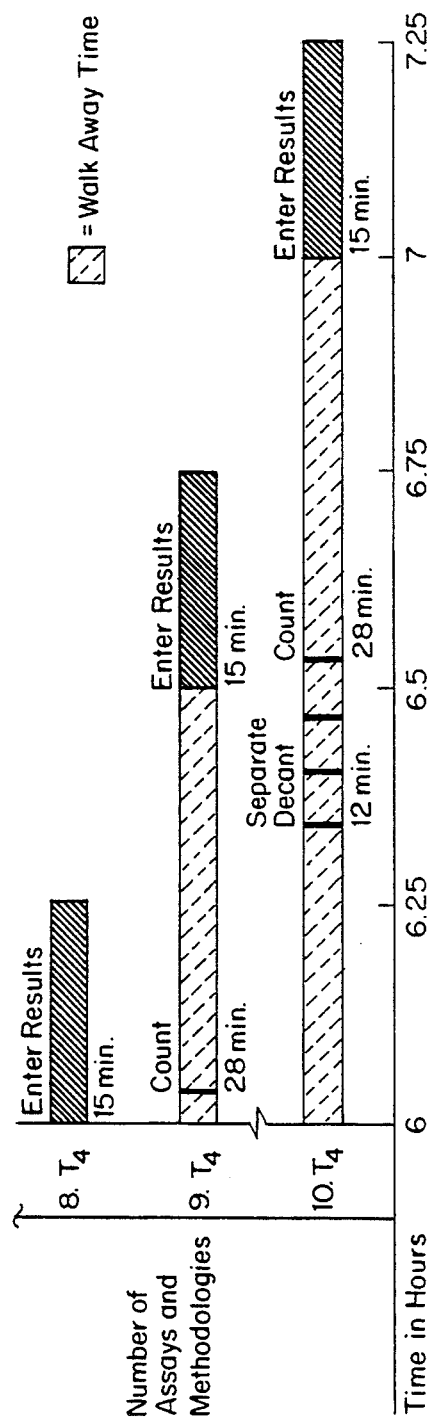
Figure 8A:
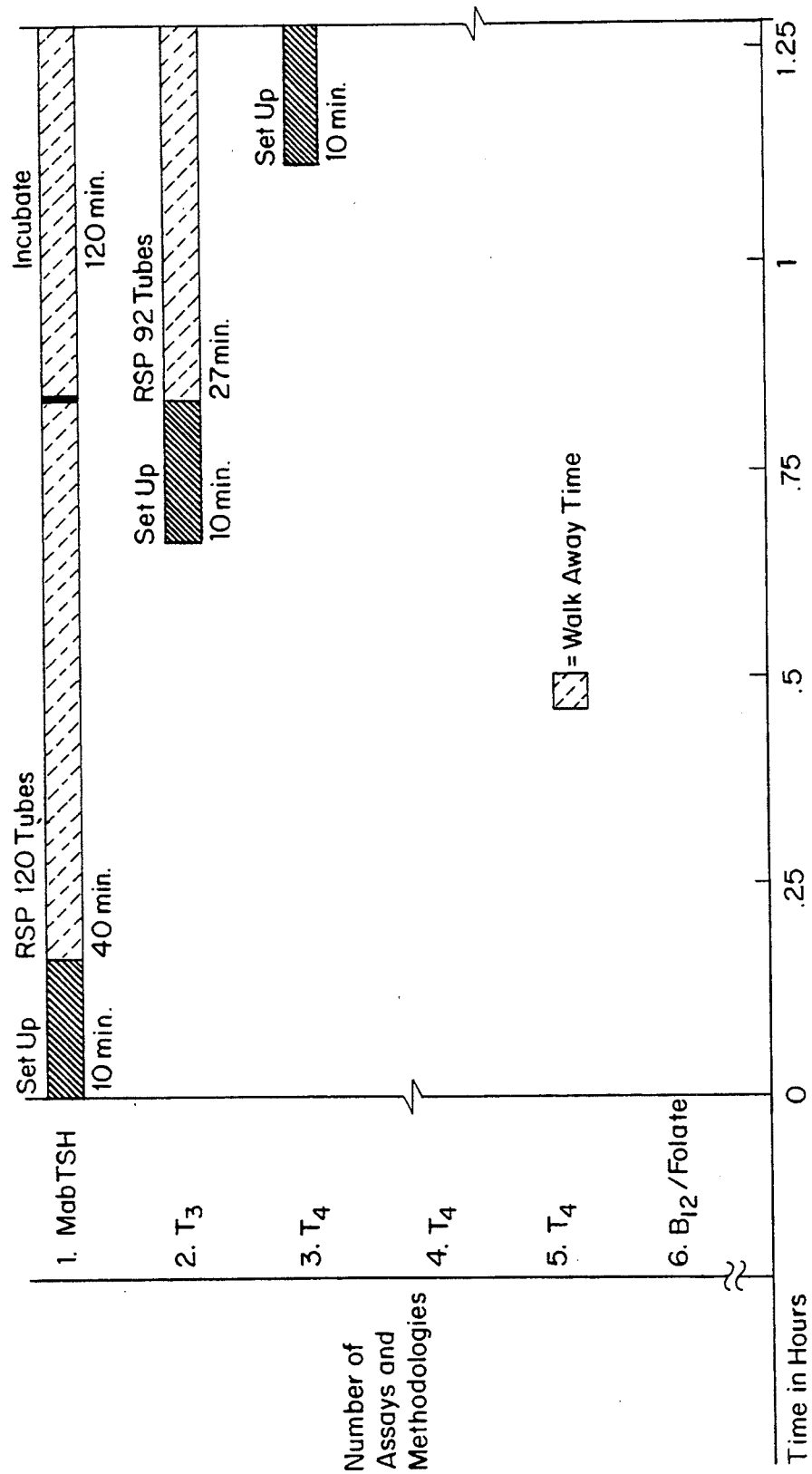
Figure 8B:
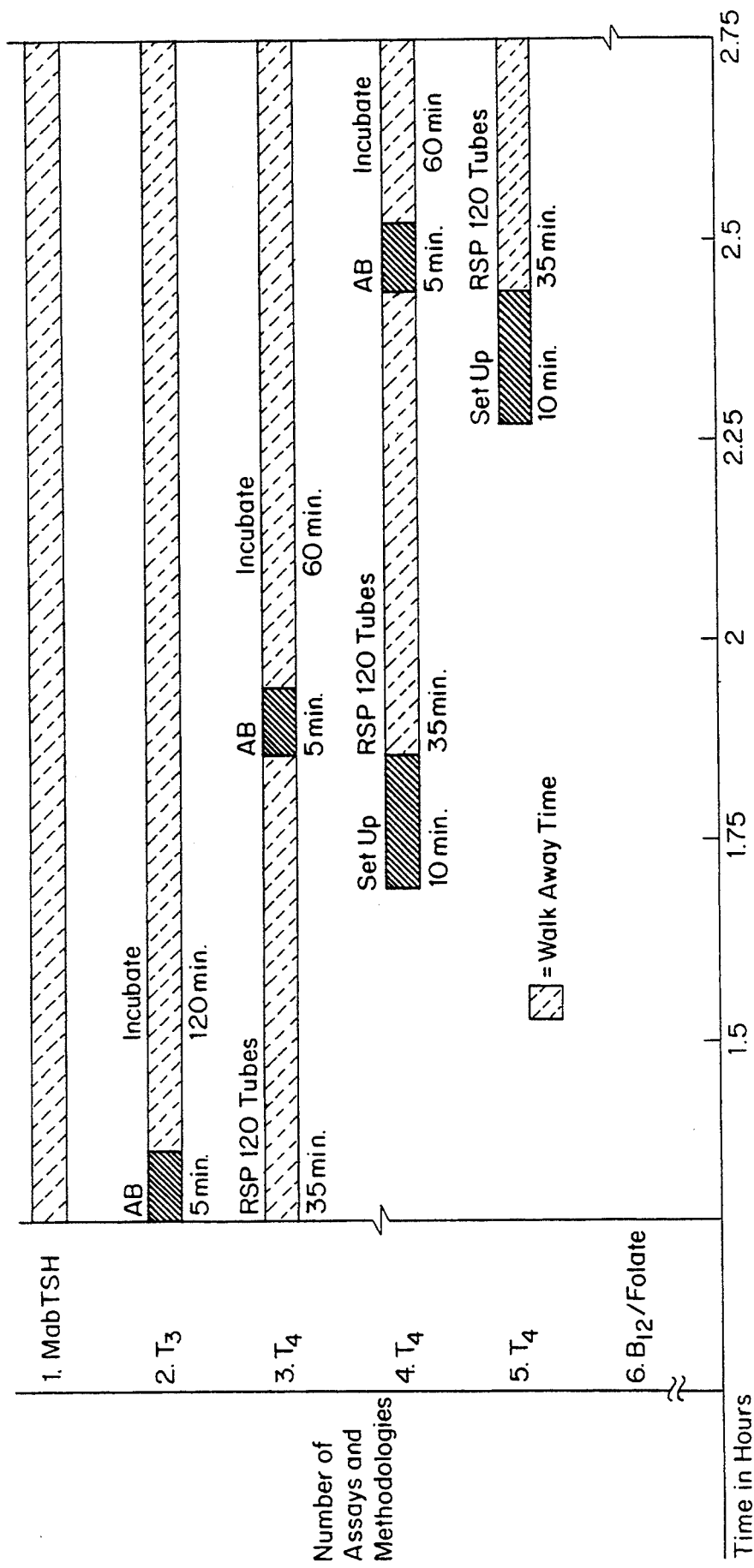
Figure 8C:
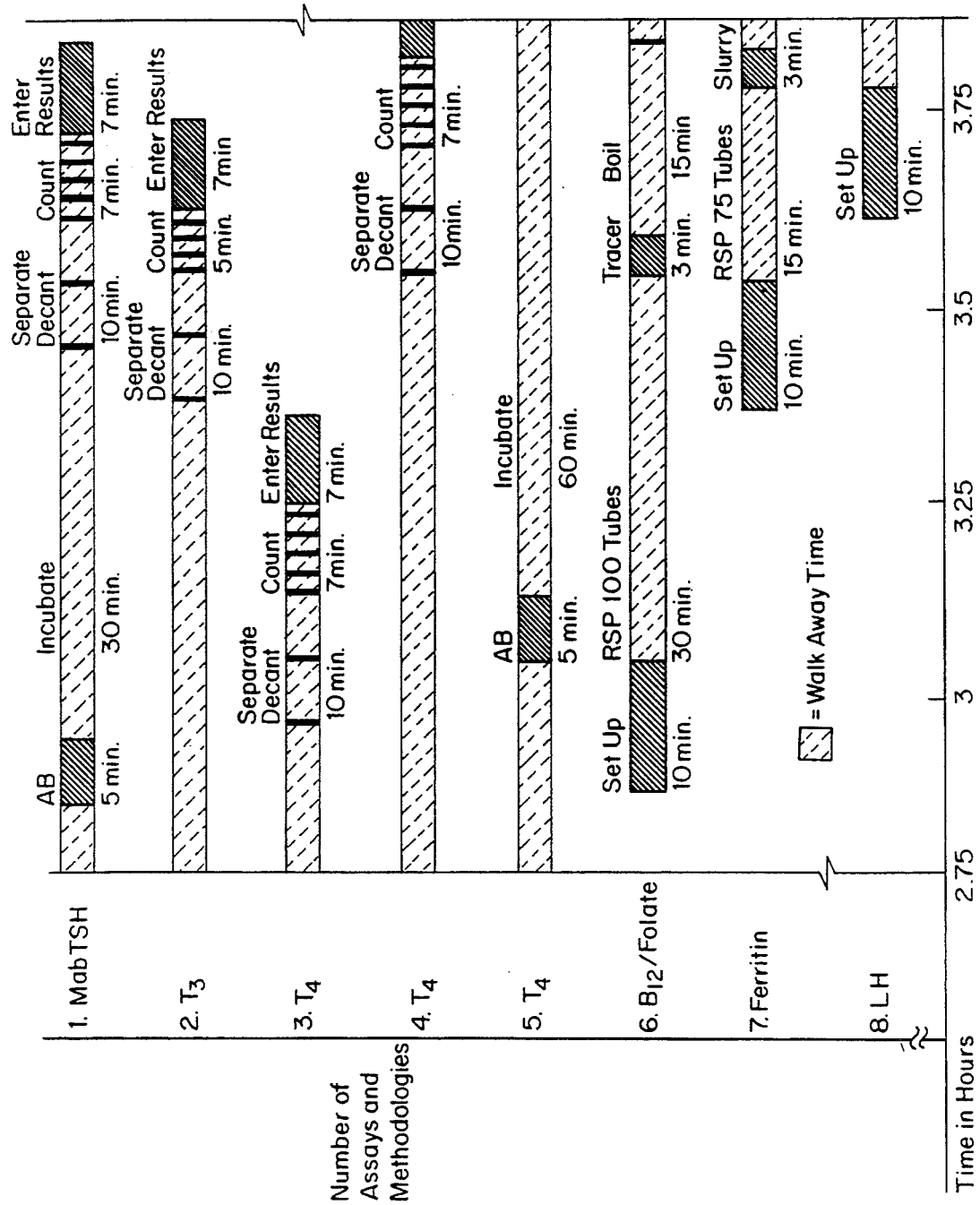
Figure 8D:
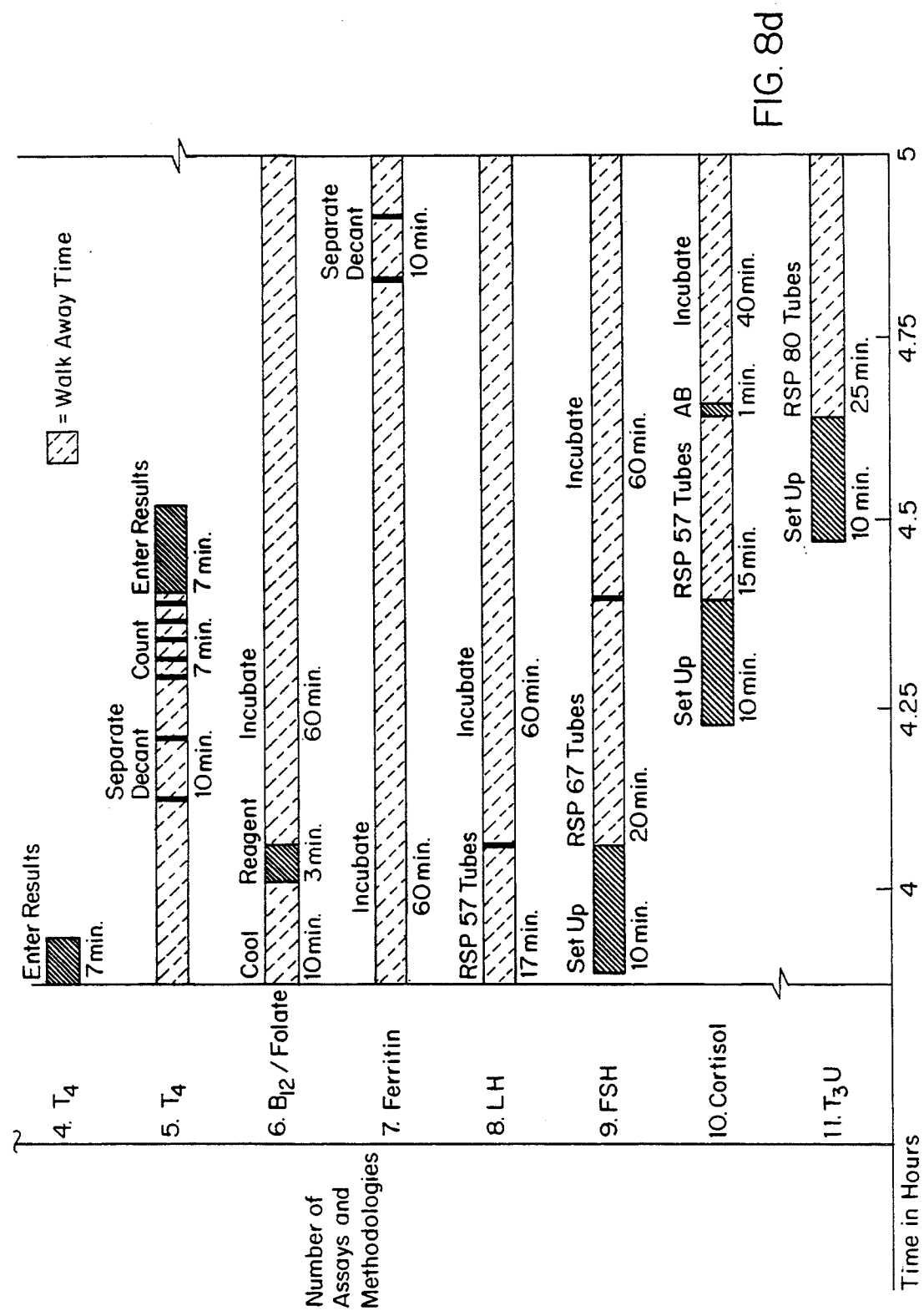
Figure 8E:
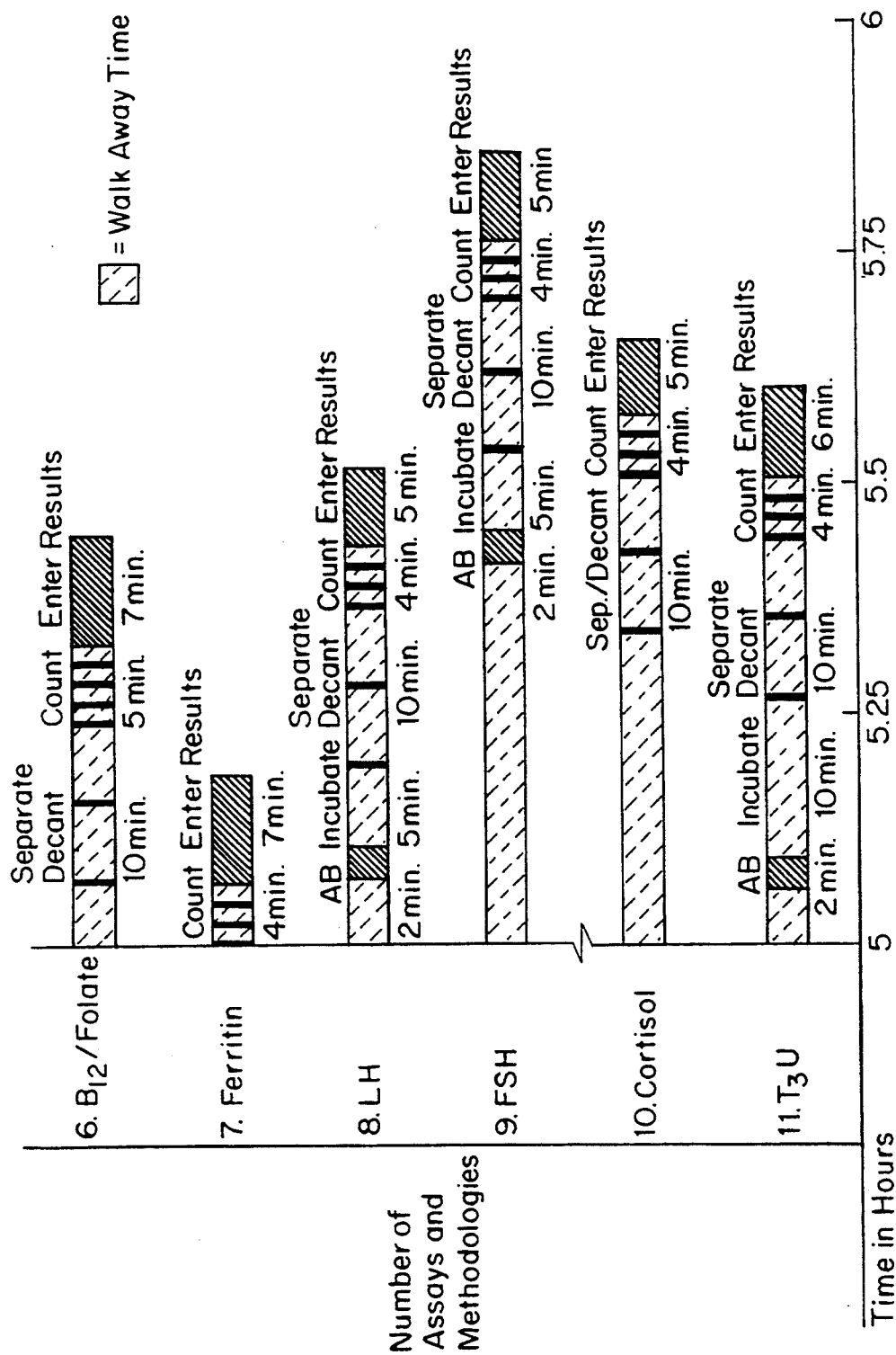

The legend of FIG. 7e provides a comparison of manual (Before implementation) and semi-automated (After implementation) processing of the same number of test samples for the selected protocol. The "After" data reflect the time saving achieved by an improved run time and a reduction in run time. A fifty percent reduction of FTEs was also achieved on implementation of the system. The case study data show a seventy-five percent reduction in the number of test results, a twelve percent decrease in run time, and a one hour improvement in turn around time.

A financial analysis is also provided in the legend. The analysis is based on an assumed labor cost for a FTE per year and a revenue generation estimate that one FTE can generate in a month. The annual labor cost saved and the increase in annual opportunity value denote the efficiency of the system as applied to a large reference laboratory.

EXAMPLE 7

Referring to FIGS. 8a–8f, the system was implemented in a medium sized reference laboratory to semi-automate its immunoassay protocols.

FIGS. 8a–8f represent a work-flow analysis diagram which illustrates the sequence for performing a total of eleven successive assays for nine selected immunoassay protocols with the system. The eleven assays generated test results for one thousand and eight test samples. The test samples included control samples, blank samples, standard samples, and patient samples.

The legend of FIG. 8f provides a comparison of manual (Before implementation) and semi-automate (After implementation) processing of the same number of test samples and selected protocols. The "After" data reflect time savings achieved by reducing run time by twenty-five percent and on a reduction in turn around time of two hours. The number of FTE's required to complete this workload could be reduced by two upon implementation of the system.

A financial analysis is also provided in the legend of FIG. 8f. The analysis is based on an assumed labor cost for a FTE per year and revenue generation estimate that one FTE can generate in a month. The annual labor cost saved and the increase in annual opportunity value denote the efficiency of the system as applied to a medium sized reference laboratory.

It is to be understood that various other modifications will be apparent to and can readily be made by those skilled in the art, given the disclosure herein, without departing from the scope and material spirit of this invention.

We claim:

1. A clinical laboratory work-flow system which semi-automates validated immunoassay and electrophoresis protocols, said system having components including:
   a. a controller for directing the operation of said system, said controller comprising:
      1. a memory unit having a plurality of computer programs stored therein, each of said programs providing format instructions for performance of a specific immunoassay or electrophoresis protocol;
      2. means for selecting a protocol;
      3. means for entering the number of test samples to be analyzed by said protocol;
      4. means for displaying the format instructions for said protocol, and;
   b. a robotic test sample transfer device comprising:
      1. a planar work-flow surface having a defined coordinate area for receiving and aligning test rack(s) and reaction medium(s); and
      2. means for transferring a volume of test sample for each test sample to be analyzed, and a volume of one or more reagent(s) from a reagent source(s) for immunoassay protocols, to a reaction medium for initiating a test reaction, the transfer(s) being in response to format instructions from said controller, and wherein said transfer(s) are free of sample carryover and free of end run effect.

2. A work-flow system as recited in claim 1, wherein said reaction medium for electrophoresis protocols comprises an electrophoresis gel.

3. A work-flow system as recited in claim 1, wherein said reaction medium for immunoassay protocols comprises a test tube.

4. A work-flow system as recited in claim 1, wherein said immunoassay protocols comprise:
   a. Thyroid Stimulating Hormone;
   b. $T_4$;
   c. Free $T_4$;
   d. $T_3$;
   e. Free $T_3$;
   f. $T_3$ uptake;
   g. $B_{12}$/Folate;
   h. Ferritin;
   i. Human Chorionic Gonadotropic Hormone;
   j. Luteinizing Hormone;
   k. Follicle Stimulating Hormone;
   l. Prolactin;
   m. Estradiol;

n. Progesterone;
o. Digoxin;
p. Cortisol;
q. Insulin;
r. Parathyroid Hormone;
s. Aldosterone;
t. CKMB; and
u. T uptake.

5. A work-flow system as recited in claim 1, wherein said electrophoresis protocols comprise:
a. Creatine Kinase Isoenzymes;
b. Lactate Dehydrogenase;
c. Serum Protein Electrophoresis;
d. Hemoglobin $A_1$;
e. Alkaline Phosphotase;
f. Lipoprotein;
g. High Density Lipoprotein;
h. Immunofixation;
i. Immunoelectrophoresis;
j. High Resolution Serum Protein;
k. Hemoglobin Alkaline; and
l. Hemoglobin Citrate.

6. A work-flow system as recited in claim 1, wherein said reaction medium for electrophoresis protocols comprises an agarose gel applied to a mylar backing.

7. A work-flow system as recited in claim 1, wherein said controller further comprises means for entering programs for additional protocols to the memory unit.

8. A work-flow system as recited in claim 1, wherein said system components further comprise one or more detection devices for determining a test result for each test reaction initiated by said transfer device.

9. A work-flow system as recited in claim 1, wherein following the initiation of said test reaction the reaction medium is removed from the work-flow surface for further processing of the reaction mixture in order to yield a test result.

10. A work-flow system as recited in claim 9, wherein said further processing includes:
a. incubation and/or;
b. adding substrate or kinetic sensitive reagent for said immunoassay protocols and/or;
c. decanting the fluid for said immunoassay protocols and/or;
d. electrophoresing the gel and/or;
e. staining the gel.

11. A work-flow system as recited in claim 1, wherein the number of test samples which can be processed by the sample transfer device for one or more immunoassay protocol(s) is limited by the controller consistent with the kinetics of the test reaction; such that the total time required to add the kinetic reagent by the device should not be longer than approximately ten percent of the incubation time for the said protocol.

12. A work-flow system as recited in claim 1, wherein said test samples comprise:
a. patient test samples;
b. control samples specific for said protocol;
c. blank samples; and
d. standard samples.

13. A work-flow system as recited in claim 1, wherein said means for selecting a protocol and means for entering the number of test samples to be analyzed is a keyboard.

14. A work-flow system as recited in claim 1, wherein said means for displaying the format instructions comprises a monitor.

15. A work-flow system as recited in claim 1, wherein following the initiation of said test reaction the test rack(s) and reaction medium are removed from the work-flow surface so that subsequent protocols are performed and wherein the performance of the protocols conform to the work-flow demands of the laboratory.

16. A work-flow system as recited in claim 8 wherein said detection devise is a gamma counter.

17. A work-flow system as recited in claim 8, wherein said detection device is a beta counter.

18. A work-flow system as recited in claim 8 wherein said detection device is a densitometer.

19. A work-flow system as recited in claim 8, wherein said detection device is capable of detecting luminescent, fluorescent, or colorometric test reaction products.

20. A work-flow system as recited in claim 1, wherein the format instructions for each protocol comprises specific speed, cutoffs, washes, air gaps, sample application, and reagent addition restrictions required for said protocol in order to achieve validated test results for diagnostic use.

21. A work-flow system as recited in claim 1, wherein said means for transferring test sample, and reagent(s) for immunoassay protocols, is one or more robotic arm(s), said arm(s) including an aspiration and sample delivery conduit.

22. A clinical laboratory work-flow system which semi-automates validated electrophoresis testing including:
a. a controller comprising:
1. a memory unit having a plurality of computer programs stored therein, each of said programs providing format instructions for performance of a specific or electrophoresis protocol;
2. means for selecting a protocol;
3. means for entering the number of test samples to be analyzed by said protocol;
4. means for displaying the format instructions for said protocol, and;
b. a robotic test sample transfer device comprising:
1. a work-flow surface having a defined coordinate area for receiving and aligning test rack(s) and reaction medium(s), said surface being adjustable, and wherein said reaction medium is an electrophoresis gel; and
2. transfer means for applying about 1 ul. of test sample onto said gel.

23. A work-flow system as recited in claim 22, wherein said electrophoresis protocols comprise:
a. Creatine Kinase Isoenzymes;
b. Lactate Dehydrogenase;
c. Serum Protein Electrophoresis;
d. Hemoglobin $A_1$;
e. Alkaline Phosphotase;
f. Lipoprotein;
g. High Density Lipoprotein;
h. Immunofixation;
i. Immunoelectrophoresis;
j. High Resolution Serum Protein;
k. Hemoglobin Alkaline; and
l. Hemoglobin Citrate.

24. A work-flow system as recited in claim 22, wherein said gel comprises and agarose gel.

25. A work-flow system as recited in claim 22, wherein said controller further comprises means for entering programs for additional protocols to the memory unit.

26. A work-flow system as recited in claim 22, wherein said system components further comprise one or more detection devices for determining a test result for each test reaction initiated by said transfer device.

27. A work-flow system as recited in claim 22, wherein following the initiation of said test reaction the reaction medium is removed from the work-flow surface for further processing of the reaction mixture in order to yield a test result.

28. A work-flow system as recited in claim 27, wherein said further processing includes:
   a. electrophoresing said gel; and
   b. staining said gel.

29. A work-flow system as recited in claim 22, wherein said test samples comprise:
   a. patient test samples; and
   b. control samples specific for said protocol.

30. A work-flow system as recited in claim 22, wherein said means for selecting a protocol and means for entering the number of test samples to be analyzed is a keyboard.

31. A work-flow system as recited in claim 22, wherein said means for displaying the format instructions comprises a monitor.

32. A work-flow system as recited in claim 22, wherein following the initiation of said test reaction the test rack(s) and reaction medium are removed from the work-flow surface so that subsequent protocols are performed and wherein the performance of the protocols conform to the work-flow demands of the laboratory.

33. A work-flow system as recited in claim 22, wherein said detection device is a densitometer.

34. A work-flow system as recited in claim 22, wherein said means for transferring test sample is a robotic arm(s), said robotic arm including an aspiration and sample delivery conduit.

* * * * *